United States Patent
Rai et al.

(10) Patent No.: US 11,149,058 B2
(45) Date of Patent: Oct. 19, 2021

(54) MULTI-FUNCTIONAL CHEMICAL AGENTS, AND THE METHOD FOR PROTEIN MODIFICATION

(71) Applicants: Department of Biotechnology, New Delhi (IN); Indian Institute of Science Education and Research Bhopal, Madhya Pradesh (IN)

(72) Inventors: Vishal Rai, Madhya Pradesh (IN); Srinivasa Rao Adusumalli, Madhya Pradesh (IN)

(73) Assignees: Department of Biotechnology, New Delhi (IN); Indian Institute of Science Education and Research Bhopal, Madyha Pradesh (IN)

( * ) Notice: Subject to any disclaimer, the term of this patent is extended or adjusted under 35 U.S.C. 154(b) by 0 days.

(21) Appl. No.: 16/085,360

(22) PCT Filed: Nov. 17, 2016

(86) PCT No.: PCT/IN2016/050408
§ 371 (c)(1),
(2) Date: Sep. 14, 2018

(87) PCT Pub. No.: WO2017/158612
PCT Pub. Date: Sep. 21, 2017

(65) Prior Publication Data
US 2019/0085020 A1 Mar. 21, 2019
US 2021/0163526 A9 Jun. 3, 2021

(30) Foreign Application Priority Data
Mar. 18, 2016 (IN) .............. 201611009537

(51) Int. Cl.
| | | |
|---|---|---|
| *C07K 1/107* | (2006.01) | |
| *C07K 14/805* | (2006.01) | |
| *C07K 1/13* | (2006.01) | |
| *C07K 1/22* | (2006.01) | |
| *C07K 1/00* | (2006.01) | |
| *C07K 1/02* | (2006.01) | |

(52) U.S. Cl.
CPC ............ *C07K 1/1075* (2013.01); *C07K 1/006* (2013.01); *C07K 1/02* (2013.01); *C07K 1/13* (2013.01); *C07K 1/22* (2013.01); *C07K 14/805* (2013.01)

(58) Field of Classification Search
CPC ........ C07K 1/006; C07K 1/02; C07K 1/1072; C07K 1/1075; C07K 1/13; C07K 1/22
See application file for complete search history.

(56) References Cited

U.S. PATENT DOCUMENTS

| | | | |
|---|---|---|---|
| 6,628,115 B2 | 9/2003 | Sasaki et al. | |
| 6,664,367 B1* | 12/2003 | Rajagopalan | ......... C07K 1/006 530/311 |
| 2005/0158370 A1 | 7/2005 | Flinn et al. | |
| 2008/0207913 A1* | 8/2008 | Breitenkamp | ......... A61K 47/34 548/237 |
| 2011/0262963 A1 | 10/2011 | Geierstanger et al. | |
| 2011/0263832 A1 | 10/2011 | Krantz et al. | |
| 2013/0071383 A1 | 3/2013 | Kofod-Hansen et al. | |
| 2013/0216479 A1 | 8/2013 | Krantz et al. | |
| 2014/0024056 A1* | 1/2014 | Chorev | .............. G01N 33/6893 435/7.93 |

FOREIGN PATENT DOCUMENTS

| | | |
|---|---|---|
| DE | 2718041 A1 | 11/1977 |
| WO | WO 2014/004278 A1 | 1/2014 |
| WO | WO 2015/200080 A1 | 12/2015 |
| WO | WO 2016/034671 A1 | 3/2016 |

OTHER PUBLICATIONS

Tsukiji et al., "Ligand-directed tosyl chemistry for protein labeling in vivo," Nat. Chem. Biol. 5, 341-43 (May 2009). (Year: 2009).*
International Search Report (ISR) for PCT/IN2016/050408; I.A. fd Nov. 17, 2016, dated Apr. 26, 2017 from the Indian Patent Office, New Delhi, India.
International Preliminary Report on Patentability (IPRP), Chapter I of the Patent Cooperation Treaty, including the Written Opinion for PCT/IN2016/050408; I.A. fd Nov. 17, 2016, dated Sep. 18, 2018, by the International Bureau of WIPO, Geneva, Switzerland.
Agrawal, D et al., "Site-specific chemical modifications of proteins," Indian Journal of Chemistry 52A, Aug.-Sep. 2013, pp. 973-991, Council of Scientific & Industrial Research, New Delhi, India.
Adusumalli, S.R. et al., "Single-Site Labeling of Native Proteins Enabled by a Chemoselective and Site-Selective Chemical Technology," J. Am. Chem. Soc. 140:15114-15123 and supplemental material (2018)—160 pages, American Chemical Society.
European Search Opinion and Supplementary European Search Report for counterpart EP Application No. 16894258.9.
Jain, P.K., et al., "Construction of a Photoactivated Insulin Depot," Angewandte Chemie, International Edition 52(5):1404-1409 (2012) Wiley-VCH.
Jain, P.K., et al., Supporting Information for "Construction of a Photoactivated Insulin Depot," Angewandte Chemie, International Edition 52(5):1404-1409 (2012)—31 pages.

\* cited by examiner

*Primary Examiner* — Theodore R. Howell
(74) *Attorney, Agent, or Firm* — Sterne, Kessler, Goldstein & Fox P.L.L.C.

(57) ABSTRACT

A multifunctional chemical agents comprising functional agents Fn1, Fn2 and linkers, for the linchpin directed (LDM), protein directed (PDPM) modifications of proteins, and Fn1 accelerated kinetic labeling by Fn2.

17 Claims, 11 Drawing Sheets

Class 4: Site selective carboxylic acid (Asp or Glu) modification

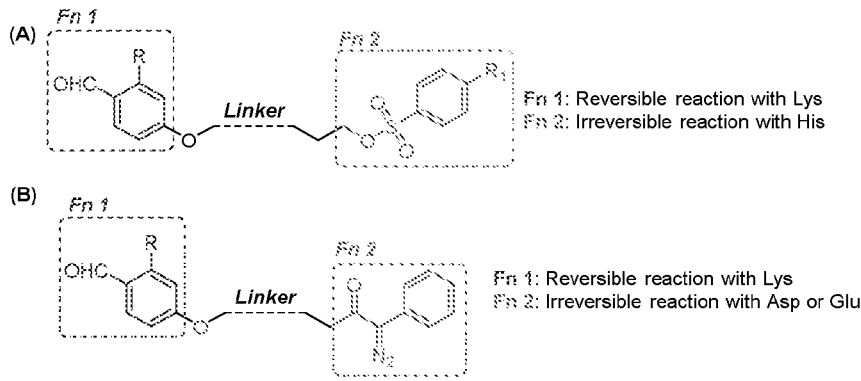

(A) Fn 1: Reversible reaction with Lys
Fn 2: Irreversible reaction with His (B) Fn 1: Reversible reaction with Lys
Fn 2: Irreversible reaction with Asp or Glu Class 5: Site-selective Tyr modification

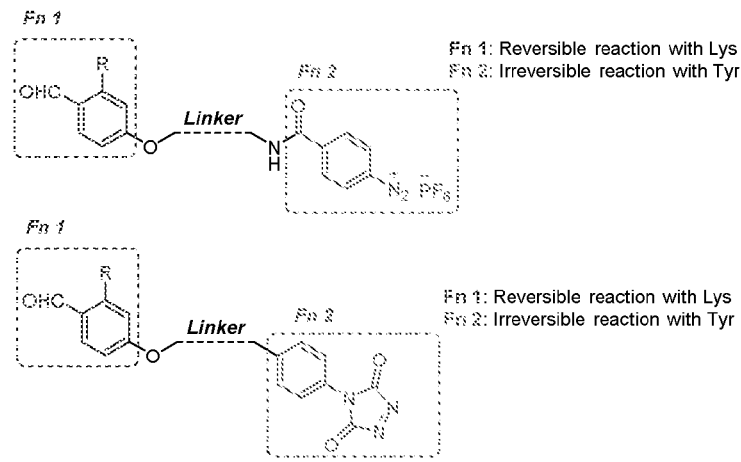

Fn 1: Reversible reaction with Lys
Fn 2: Irreversible reaction with Tyr

Fn 1: Reversible reaction with Lys
Fn 2: Irreversible reaction with Tyr

Class 6: Site-selective Arg modification

Fn 1: Reversible reaction with Lys
Fn 2: Irreversible reaction with Arg

Class 7: Site-selective Met modification

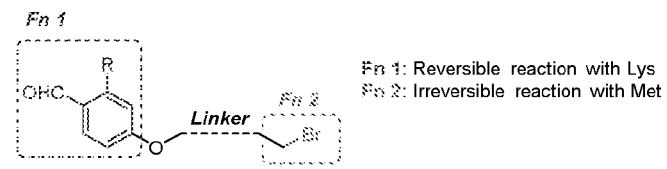

Fn 1: Reversible reaction with Lys
Fn 2: Irreversible reaction with Met

Figure 1.

Class 1: General linkers
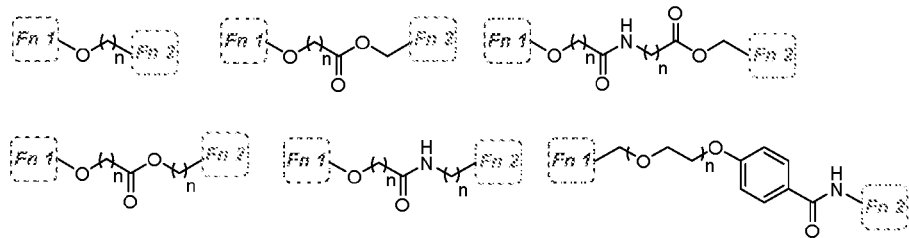
Class 2: PEG linkers
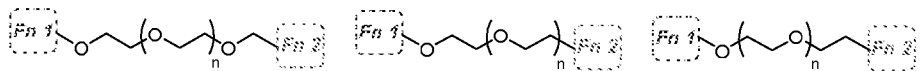
Class 3: β-turn linkers
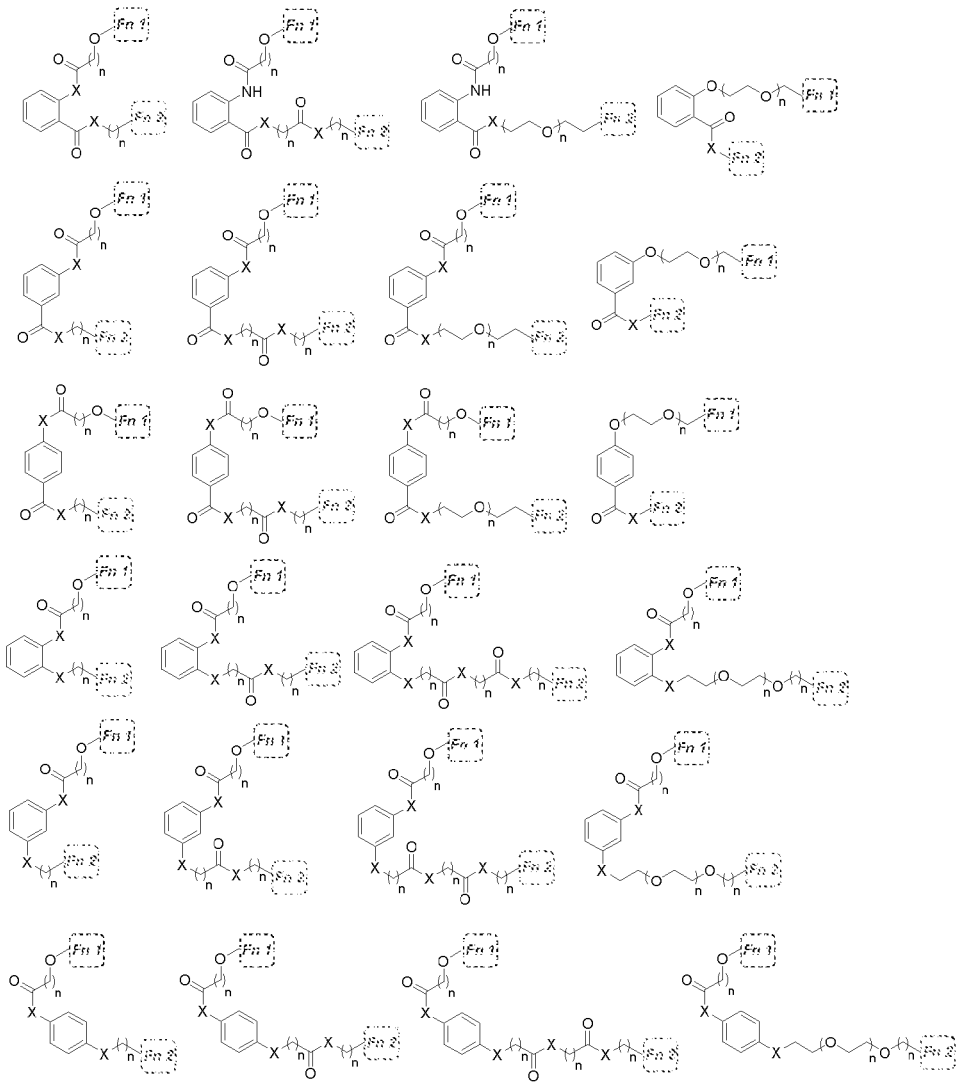
Figure 2.

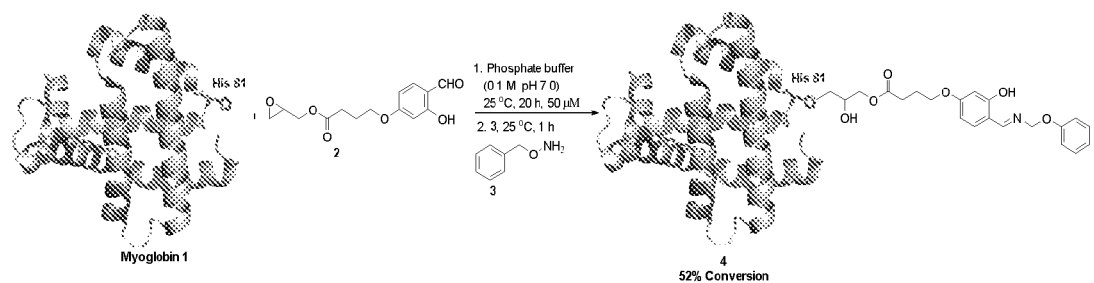
Scheme 1. Lys directed His modification
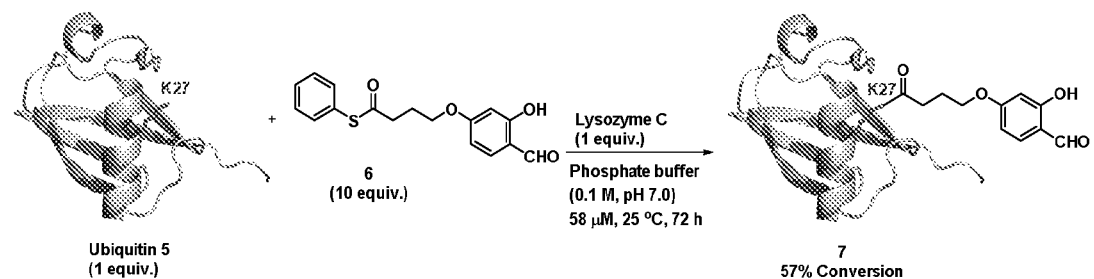
Scheme 2. Lysozyme C directed Ubiquitin modification
Figure 3.

Figure 4:
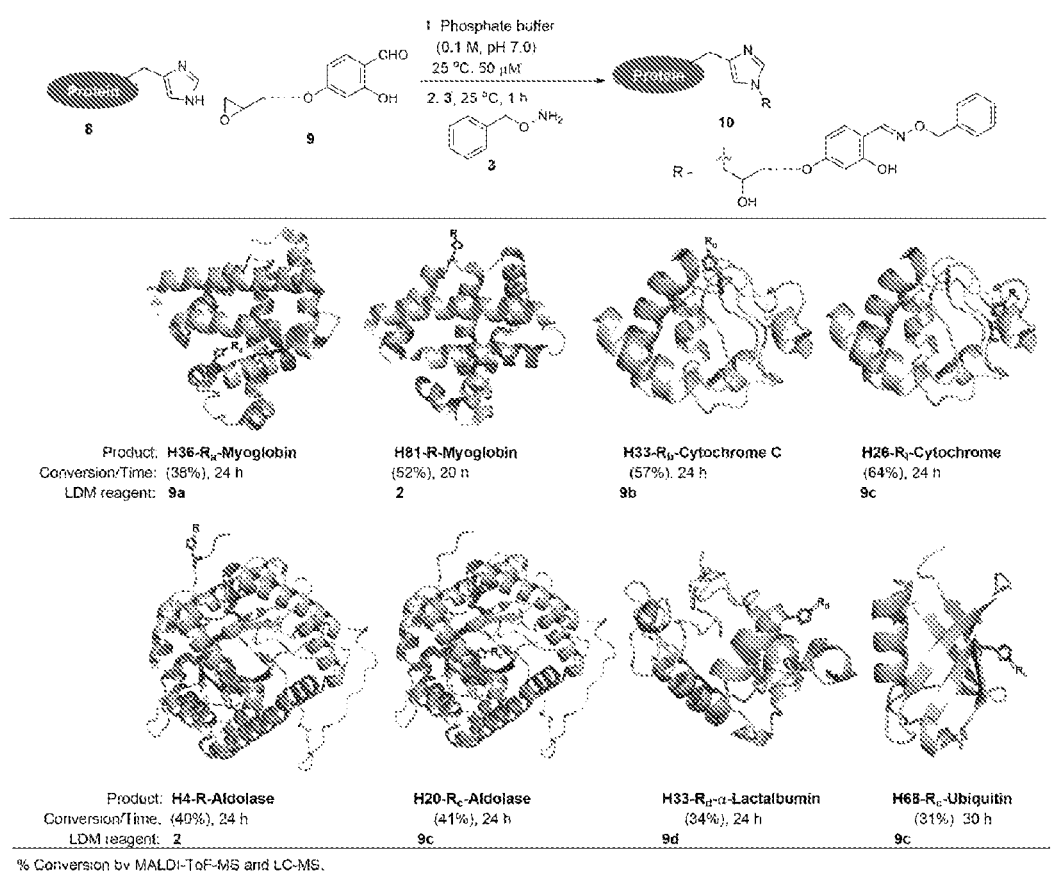

Figure 4. Site-selective native protein modification enabled by LDM

Figure 5:
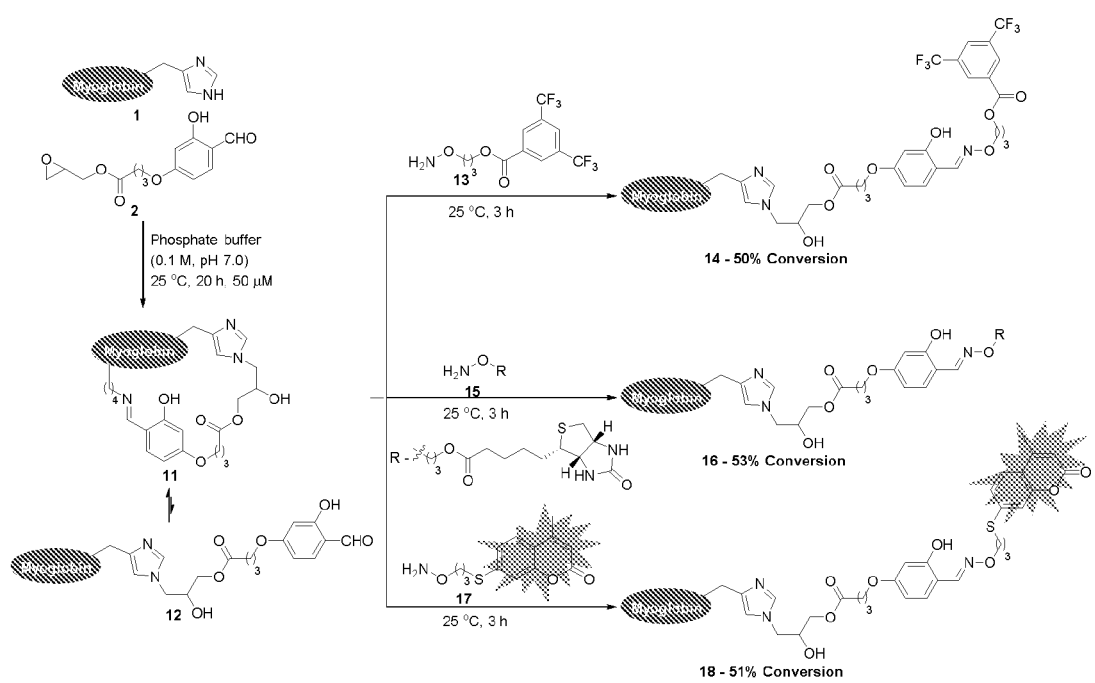

Figure 5. Installation of tags through oxime formation

Figure 6:
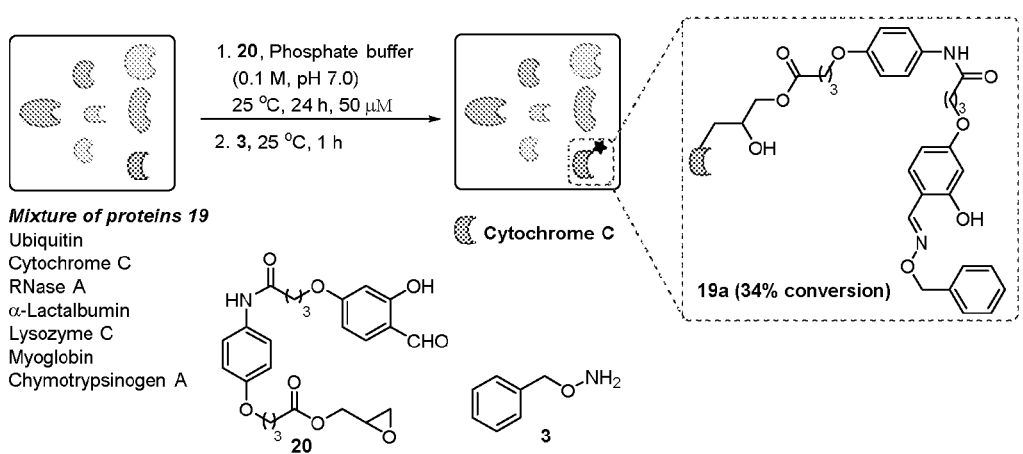

Figure 6. Single site-single protein modification in a protein mixture

Figure 7:
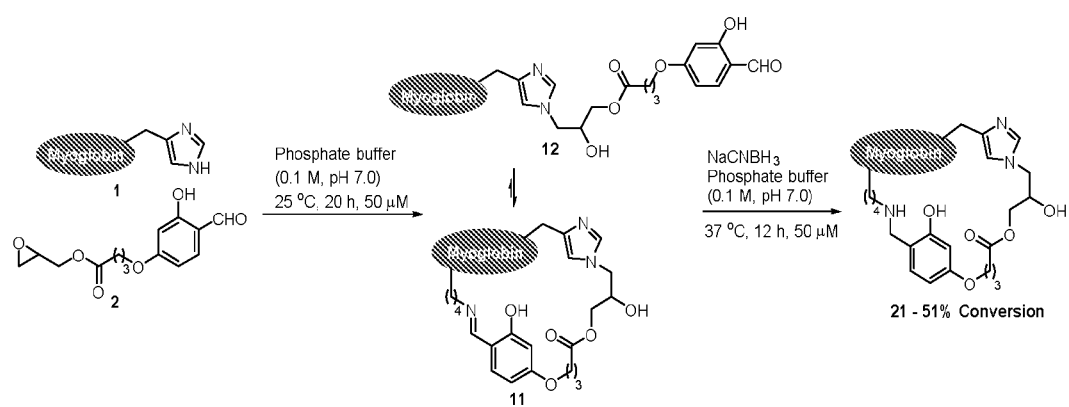

Figure 7. Protein cyclization

Figure 8:
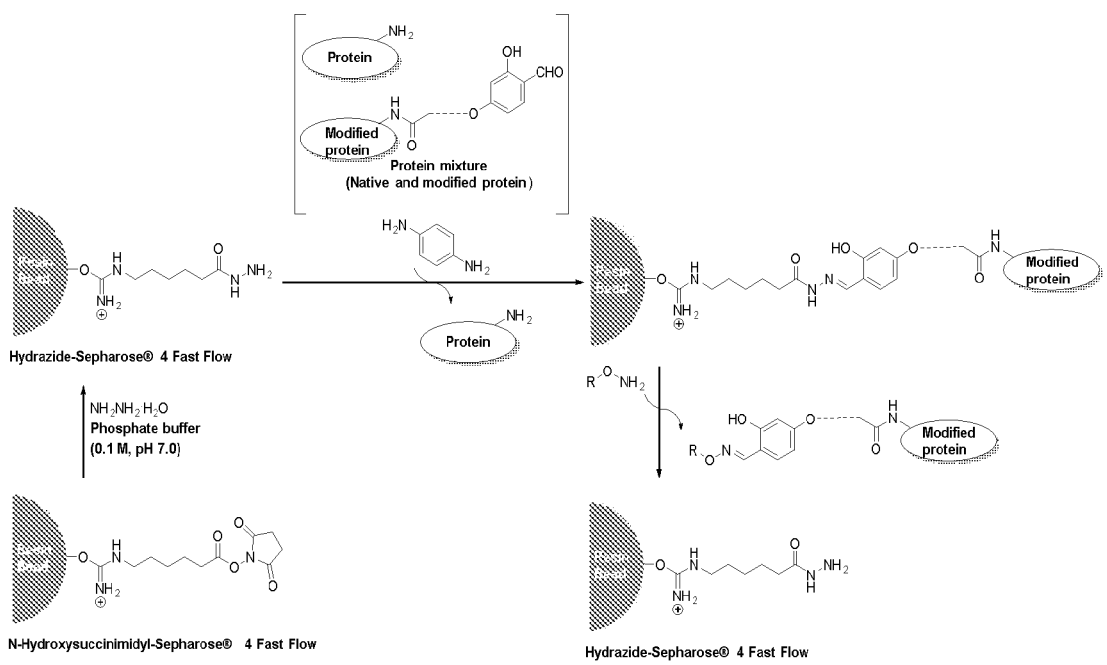

Figure 8. Purification of modified protein from protein mixture using hydrazide-activated resin

Figure 9:
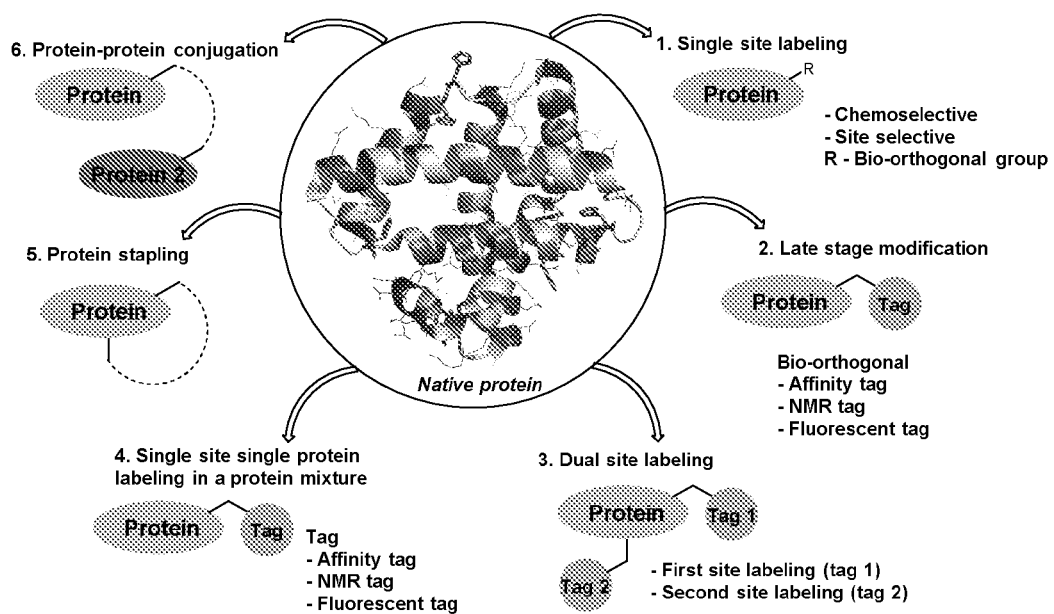

Figure 9. Overview of LDM technology

US 11,149,058 B2

MULTI-FUNCTIONAL CHEMICAL AGENTS, AND THE METHOD FOR PROTEIN MODIFICATION

FIELD OF INVENTION

The invention is in the field of biotechnology with specific reference to site selective modification of proteins.

BACKGROUND OF THE INVENTION

The diversity of structure and function of proteins emerges from their co-translational and post-translational modification. In efforts to mimic this process of nature, synthetic modification of protein has emerged as a wonder tool. It offers a broad range of applications for proteins being used from probes to therapeutics. The ability in developing a synthetic parallel of the natural system is challenging as the site-specific modification of proteins requires controlled condition which is limited by the chemistry available. Further, the need for molding the operating parameters and reactions for modification to a near biologically similar condition becomes relevant so as not to disrupt the protein architecture or function. Over many decades, a number of methodologies have emerged for modifying both the natural and unnatural amino acid residues. Proteins consist of several nucleophilic functional groups raising challenges for differentiation based on their selective reactivity. Therefore, the focus is on incorporating unnatural amino acids by manipulation of the genetic machinery of cells. The task of precise labeling of native proteins is still challenging and would require multiple approaches to meet the desired targets. The site-directed mutagenesis route works well but operates through an engineered protein which is a huge limitation. A native protein can be labeled in a site-selective transformation through affinity guided approach. However, it is bogged down by the requirement of a specific affinity tag as a pre-requisite, whereas the chemoenzymatic methods have very limited scope of application. At present, chemoselective and site-selective protein labeling is typically achieved through engineered proteins. An unnatural amino acid(s) is incorporated in these proteins through site-directed mutagenesis and utilized for bio-orthogonal chemical transformation. Needless to mention, that this technique can't be used with native proteins. For example, antibody drug conjugates (ADCs) for directed therapeutics require site-selective protein labeling for access to homogeneous ADCs.

The engineered monoclonal antibody approach is not practical; hence, both the approved drugs are synthesized using chemical methods. However, in absence of an enabling technology, both the approved drugs are sold as heterogeneous mixtures [brentuxinab vedotin (Seattle Genetics; anti-CD30mAb, PAB linker, MMAE drug) and adotrastuzumab emtansine (Genentech; anti-HER2 mAb, SMCC linker, maytansine drug)].

Single site modification of protein would require addressing challenges related to chemoselectivity and site-selectivity (occasionally regioselectivity). A pre-requisite for a successful method would be to have a chemoselective modification that can differentiate one functional group from the other. The challenge originates from the presence of multiple types of amino acids with nucleophilic side chain functional groups. This is further complicated by the presence of several copies of each amino acid. It is a grand challenge to distinguish one residue from multiple copies of an amino acid present in protein for a site-selective modification. For site-selective protein backbone modification (other than N-terminus) with an un-engineered protein, ligand directed labeling is known. The limitation of this method is that it works well for cases where a ligand is known for binding selectively to the site of interest. For all the other cases, this method would not find any use. A chemical agent and method to distinguish one residue from multiple copies of an amino acid present in protein for a site-selective modification would find immense utility in diverse areas of chemistry and biology.

OBJECT OF THE INVENTION

The object of the invention is to develop multifunctional chemical agents for site selective modification of the reactive groups of the protein backbone of native or un-engineered proteins, Fab, antibody or any functional biological molecule. Another object of the invention is to develop a method for site selective modification of native or un-engineered proteins using the multifunctional chemical agents and where reactivity parameters are regulated by the multifunctional chemical agents which allow site selective modifications.

Another object of the invention is making the functional group amenable to bio-orthogonal late stage chemical transformation after site selective modification of protein, Fab or an antibody. By this transformation any tag of interest can be attached that can serve as reporter (affinity tags, fluorophores, NMR tags, PEG, drugs etc), function modulator, anchor for surface binding etc. The transformations predominantly regulate the chemoselectivity and site-selectivity. They enable protein labeling, protein cyclization, protein-protein conjugation, enzyme-protein conjugation, and enzyme-antibody conjugation.

BRIEF DESCRIPTION OF THE DRAWINGS AND FIGURES

FIG. 1 shows various classes of multifunctional chemical agents for site selective protein modification FIG. 2 shows various linkers of the multifunctional chemical agents FIG. 3 (Scheme 1): illustrates modification of native protein by multifunctional agents using Linchpin directed modification (Lys directed His modification).

FIG. 3 (Scheme 2): illustrates protein directed protein modification (Lysozyme C directed ubiquitin modification).

FIG. 4: illustrates site selective modification of native proteins using the LDM reagents FIG. 5: depicts late stage modification of proteins by installation of tags through oxime formation.

FIG. 6: depicts single site modification of protein in a protein mixture using the LDM reagents.

FIG. 7: shows protein cyclization using LDM reagents

FIG. 8: schematic diagram of the steps of purification of modified protein from the protein mixture using hydrazide-activated resin.

FIG. 9: Illustration of the LDM technology

Figure 10:
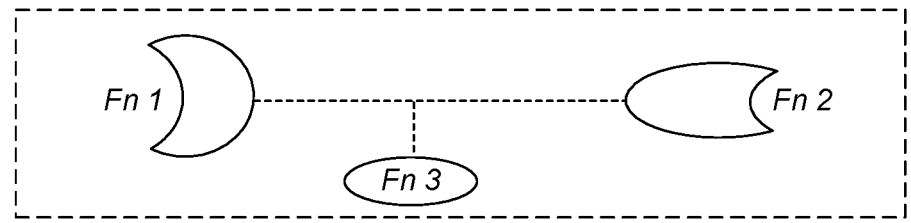

FIG. 10: shows the structure of the multifunctional chemical agent made up of Fn1, Fn2, and Fn3.

Figure 11:
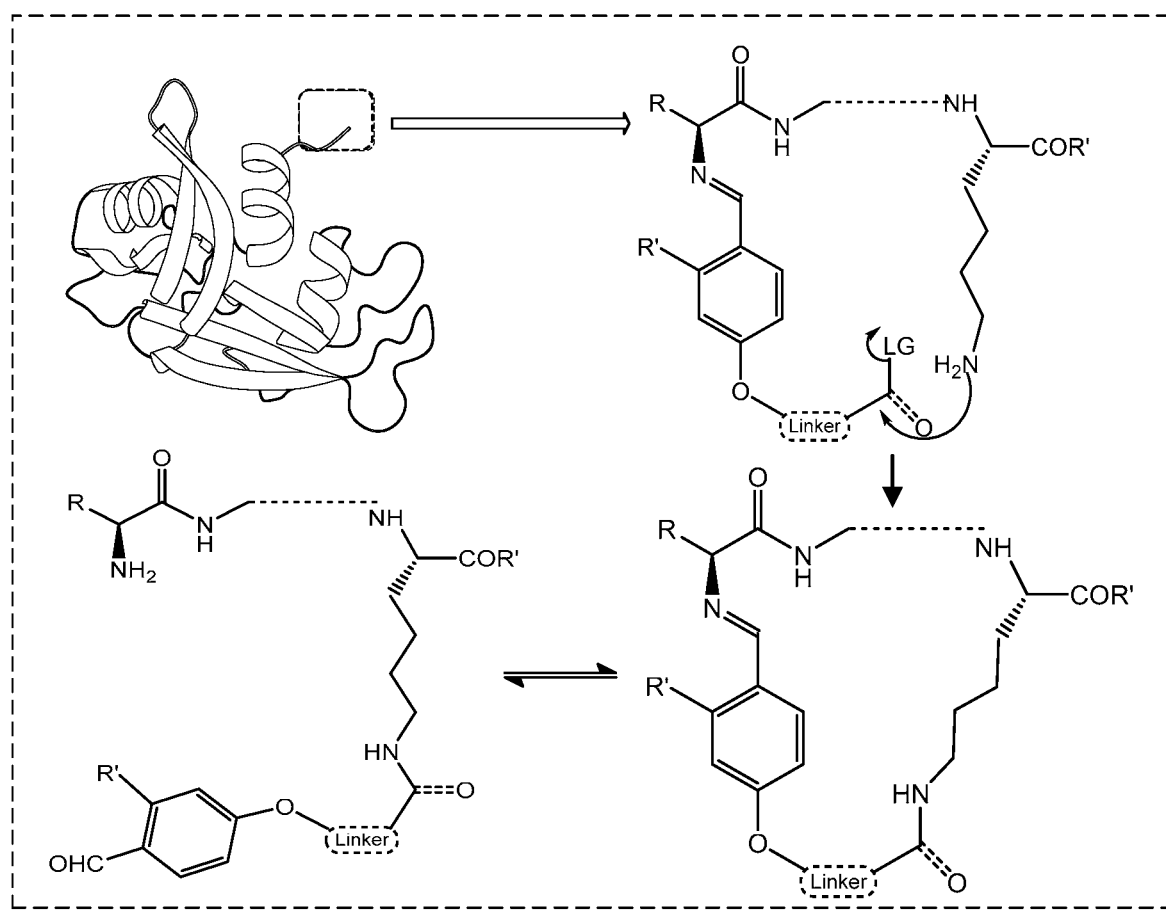

FIG. 11: illustrates a linchpin directed modification (LDM).

Figure 12:
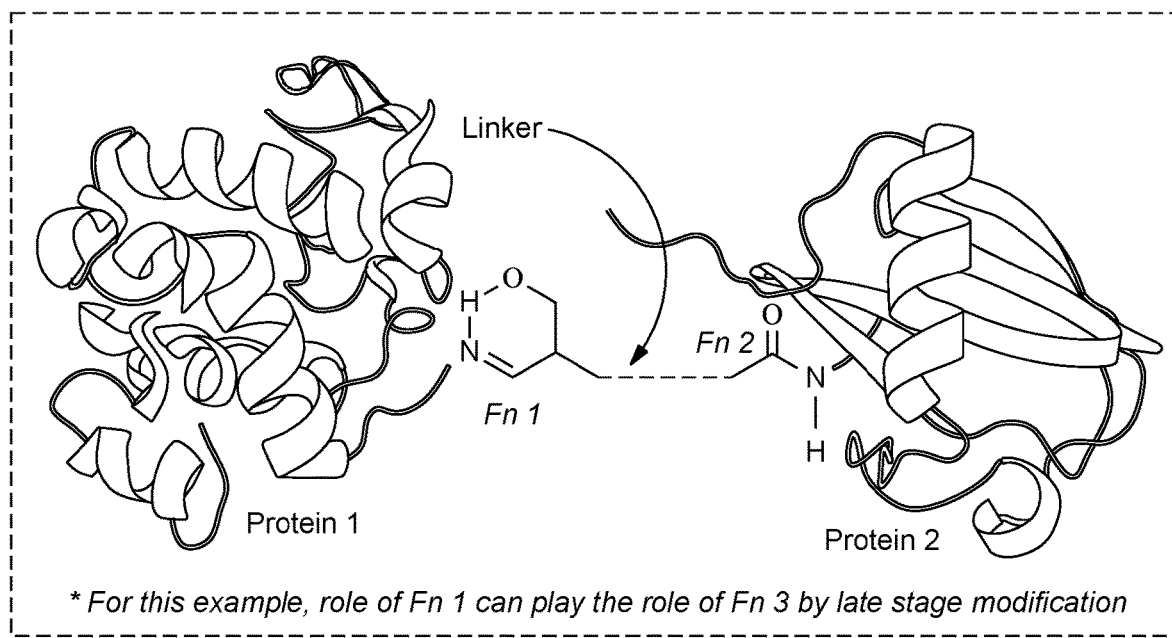

FIG. 12: illustrates a protein directed protein modification (PDPM).

DETAILED DESCRIPTION OF THE INVENTION

Accordingly, the present invention is for multifunctional chemical agents for site selective modification of the reactive groups of the protein backbone of native or un-engineered proteins or any functional biological molecule.

Further, the invention is for a method for site selective modification of native or un-engineered proteins using the multifunctional chemical agents and where reactivity parameters are regulated by the multifunctional chemical agents which allow site selective modifications.

The methods of the invention are effective with native proteins eliminating the requirement of pre-protein engineering and introduction of un-natural amino acids. The site specific modification is also a chemoselective modification.

The multifunctional chemical agent essentially has two or more functional groups which allow site specific modification of proteins or any functional biological molecule by a combination of reversible and irreversible transformations.

These multifunctional chemical agents offer a chemical method for chemoselective and site-selective modification of proteins and can be extended to any multifunctional molecules.

A multifunctional chemical agent is a four component agent wherein the first component Fn 1, or a functional group 1 that allows (a) reversible (or irreversible) modification of a reactivity hotspot (protein residue) like α-amine or single residues or (b) chemoselective reversible (or irreversible) modification of all the accessible residues of one amino acid. Fn 2, or functional group 2 allows irreversible modification of a protein residue guided by the site of attachment of Fn 1. The third component, i.e. linker, is for connecting Fn 1 and Fn 2. The length, geometry and rigidness/flexibility of the linker are essential in regulating the linched Fn 1 guided site-selective modification of proteins by Fn 2. The fourth component Fn 3 is required for attachment of affinity tag or purification tag. In some multifunctional chemical agents, Fn 1 is capable of offering the function of Fn 3. In some of the reagents Fn 3 is a functional group that is unreactive towards native amino acid residues, Fn 1 and Fn 2, e.g. terminal alkyne, cyclooctyne etc.

Fn 1 is Selected from

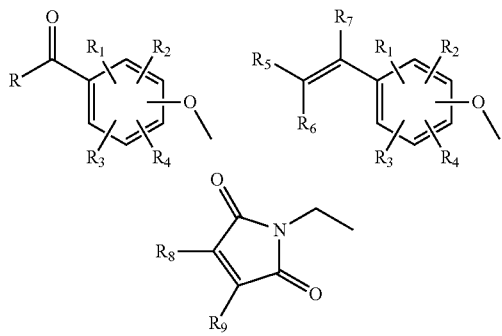

Fn 2 is Selected from

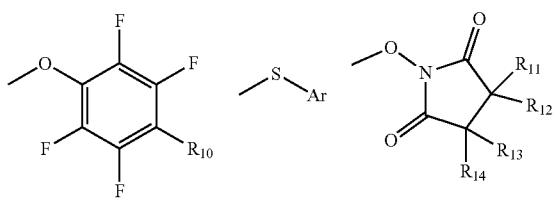

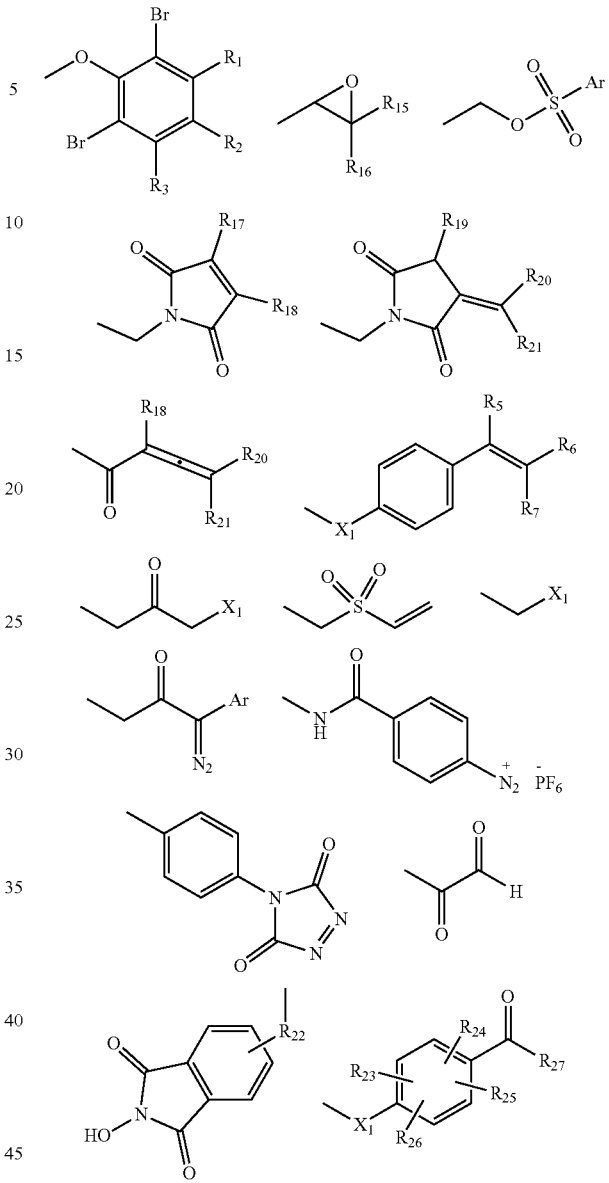

Ar = Aryl group; $X_1$ = halide, leaving group or heteroatom

Linkers are Selected from

General linkers

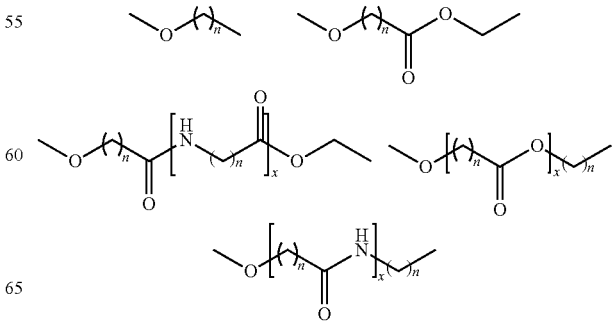

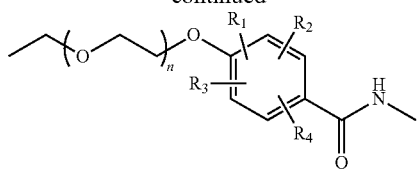
PEG linkers
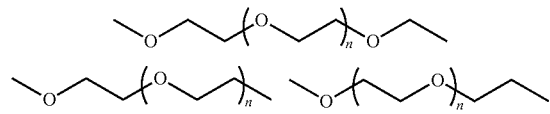
β-turn linkers
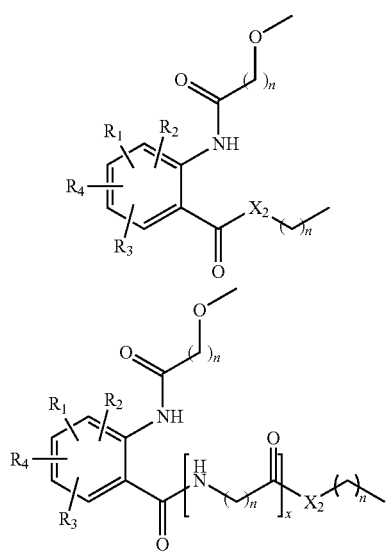
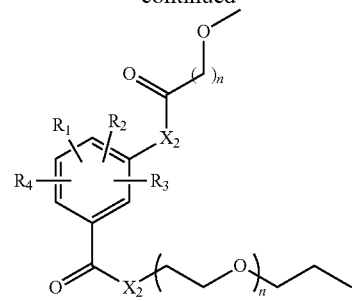
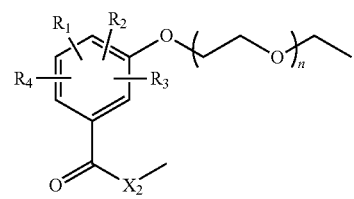
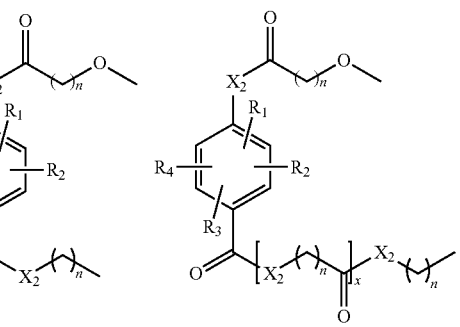
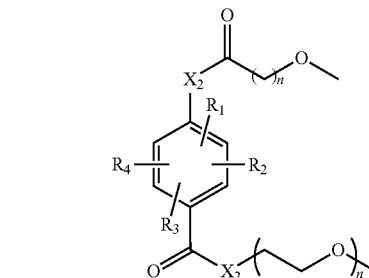
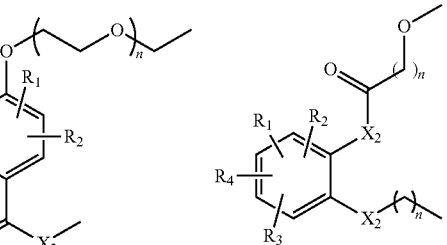
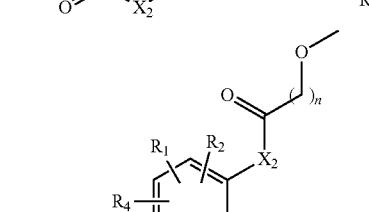

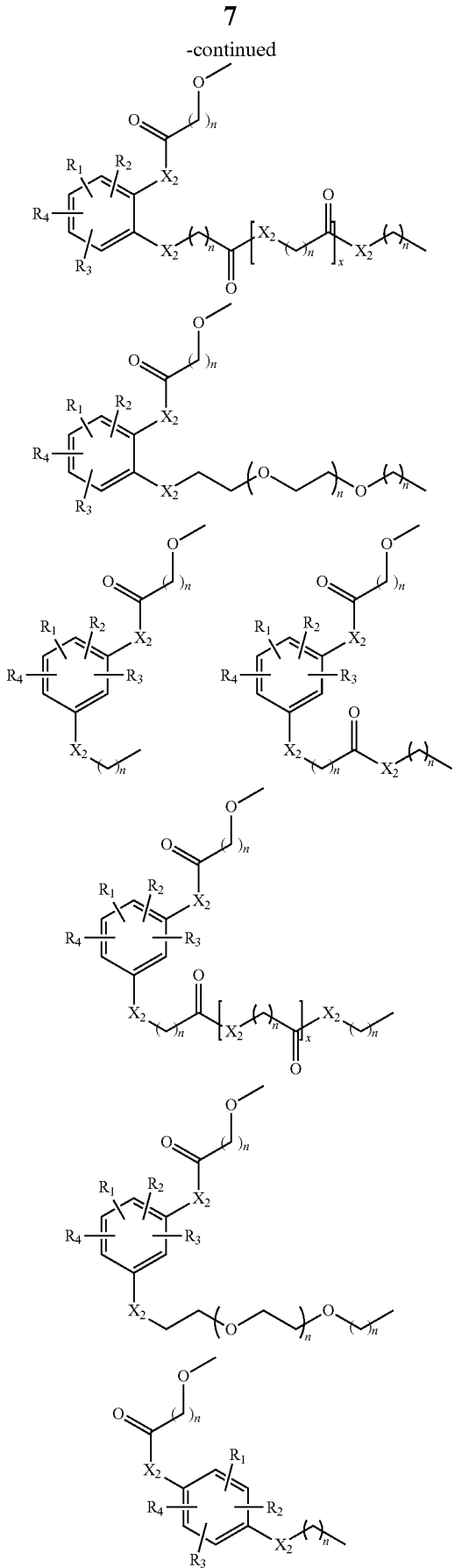
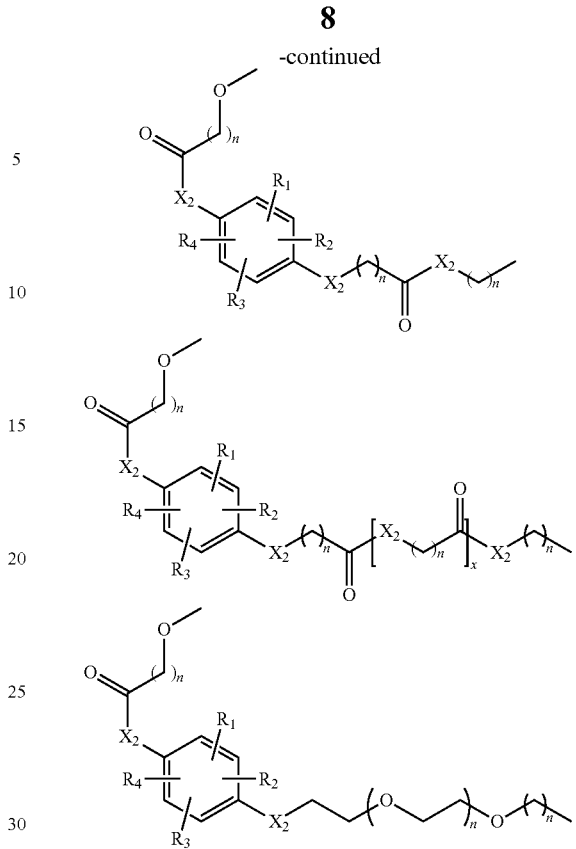

For Fn1, Fn2 and linker: $X_1$=halides, leaving group or heteroatoms, $X_2$=O or NH n=1-10, x=1-10, R is independently selected from H; alkyl; cycloalkyl; aryl and $R_1$, $R_2$, $R_3$ and $R_4$ are independently selected from H; hydroxyl; —B(OR$^{1*}$)(OR$^{1**}$) wherein R$^{1*}$ and R$^{1**}$ are independently selected from H; alkyl; lower alkyl; cycloalkyl; aryl; heteroaryl; alkenyl; heterocycle; halides; nitro; —C(O)OR$^{2*}$ wherein R$^{2*}$ is selected from H, alkyl; cycloalkyl and aryl; —C(O)NR$^{3}$R$^{3*}$, wherein R$^{3}$ and R$^{3*}$ are independently selected from H, alkyl; cycloalkyl and aryl; —CH$_2$C(O)R$_a$, wherein R$_a$ is selected from —OH, lower alkyl, cycloalkyl; aryl, -lower alkyl-aryl, -cycloalkyl-aryl; or —NR$_b$R$_c$, where R$_b$ and R$_c$ are independently selected from H, lower alkyl, cycloalkyl; aryl or -lower alkyl-aryl; —C(O)R$_d$, wherein R$_d$ is selected from lower alkyl, cycloalkyl; aryl or -lower alkyl-aryl; or -lower alkyl-OR$_e$, wherein R$_e$ is a suitable protecting group or OH group, $R_5$, $R_6$, and $R_7$ are independently selected from H; nitro; cyano; halides; alkyl; cycloalkyl; aryl and C(O)OR$^{4*}$ wherein R$^{4*}$ is selected from H, alkyl; cycloalkyl and aryl; —C(O)NR$^{5}$R$^{5*}$, wherein R$^{5}$ and R$^{5*}$ are independently selected from H, alkyl; cycloalkyl and aryl, $R_8$ and $R_9$ are independently selected from H; halides; alkyl; cycloalkyl and aryl, $R_{10}$ is selected from H; nitro; cyano; halides; alkyl; cycloalkyl; aryl and C(O)OR$^{6*}$ wherein R$^{6*}$ is selected from H, alkyl; cycloalkyl and aryl; —C(O)NR$^{7}$R$^{7*}$, wherein R$^{7}$ and R$^{7*}$ are independently selected from H, alkyl; cycloalkyl and aryl, $R_{11}$, $R_{12}$, $R_{13}$ and $R_{14}$ are independently selected from H; alkyl; cycloalkyl; aryl and —SO$_3$R$^{8*}$ wherein R$^{8*}$ is selected from H; Na. $R_{15}$ and $R_{16}$ are independently selected from H; alkyl; cycloalkyl; aryl and C(O)OR$^{9*}$ wherein R$^{9*}$ is selected from H, alkyl; cycloalkyl and aryl; —C(O)NR$^{10}$R$^{10*}$, wherein R$^{10}$ and R$^{10*}$ are independently selected from H, alkyl; cycloalkyl and aryl, $R_{17}$ and $R_{18}$ are independently selected from H; halides; alkyl; cycloalkyl and aryl, $R_{19}$, $R_{20}$, and $R_{21}$ are independently selected from H; alkyl; aryl and C(O)OR$^{11*}$ wherein R$^{11*}$ is selected from H, alkyl; cycloalkyl and aryl; —C(O) NR$^{12}$R$^{12*}$, wherein R$^{12}$ and R$^{12*}$ are independently selected from H, alkyl; cycloalkyl and aryl; $R_{22}$ is selected from H; alkyl; cycloalkyl; aryl; —NR$^{13*}$R$^{13**}$, wherein R$^{13*}$ and R$^{13}$ are independently selected from H, alkyl; cycloalkyl; aryl and —COR$^{14*}$ wherein R$^{14***}$ is alkyl; cycloalkyl and aryl; $R_{23}$, $R_{24}$, $R_{25}$, $R_{26}$ and $R_{27}$ are selected from H; alkyl; lower alkyl; cycloalkyl; aryl; heteroaryl; alkenyl; heterocycle; halides; OR$^{15*}$ wherein R$^{15*}$ is selected from H, alkyl; cycloalkyl and aryl. All the $R_n$ groups are optionally substituted at one or more substitutable positions with one or more suitable substituents.

The term "suitable substituent" is meant to include independently H; hydroxyl; cyano; alkyl, such as lower alkyl, such as methyl, ethyl, propyl, n-butyl, t-butyl, hexyl and the like; alkoxy, such as lower alkoxy such as methoxy, ethoxy, and the like; aryloxy, such as phenoxy and the like; vinyl; alkenyl, such as hexenyl and the like; alkynyl; formyl; haloalkyl, such as lower haloalkyl which includes $CF_3$, $CCl_3$ and the like; halide; aryl, such as phenyl and napthyl; heteroaryl, such as thienyl and furanyl and the like; amide such as C(O)NRR*, where R and R* are independently selected from lower alkyl, aryl or benzyl, and the like; acyl, such as C(O)—$C_6H_5$, and the like; ester such as —C(O)OCH$_3$ the like; ethers and thioethers, such as O-Bn and the like; thioalkoxy; phosphino; and —NR$_b$R$_c$, where R$_b$ and R$_c$ are independently selected from lower alkyl, aryl or benzyl, and the like. It is to be understood that a suitable substituent as used in the context of the present invention is meant to denote a substituent that does not interfere with the formation of the desired product by the processes of the present invention.

As used in the context of the present invention, the term "lower alkyl" as used herein either alone or in combination with another substituent means acyclic, straight or branched chain alkyl substituent containing from one to six carbons and includes for example, methyl, ethyl, 1-methylethyl, 1-methylpropyl, 2-methylpropyl, and the like. A similar use of the term is to be understood for "lower alkoxy", "lower thioalkyl", "lower alkenyl" and the like in respect of the number of carbon atoms. For example, "lower alkoxy" as used herein includes methoxy, ethoxy, t-butoxy.

The term "alkyl" encompasses lower alkyl, and also includes alkyl groups having more than six carbon atoms, such as, for example, acyclic, straight or branched chain alkyl substituents having seven to ten carbon atoms.

The term "aryl" as used herein, either alone or in combination with another substituent, means an aromatic monocyclic system or an aromatic polycyclic system. For example, the term "aryl" includes a phenyl or a napthyl ring, and may also include larger aromatic polycyclic systems, such as fluorescent (eg. anthracene) or radioactive labels and their derivatives.

The term "heteroaryl" as used herein, either alone or in combination with another substituent means a 5, 6, or 7-membered unsaturated heterocycle containing from one to 4 heteroatoms selected from nitrogen, oxygen, and sulphur and which form an aromatic system. The term "heteroaryl" also includes a polycyclic aromatic system comprising a 5, 6, or 7-membered unsaturated heterocycle containing from one to 4 heteroatoms selected from nitrogen, oxygen, and sulphur.

The term "cycloalkyl" as used herein, either alone or in combination with another substituent, means a cycloalkyl substituent that includes for example, but is not limited to, cyclopropyl, cyclobutyl, cyclopentyl, cyclohexyl and cycloheptyl. The term also involves "cycloalkyl-alkyl-" that means an alkyl radical to which a cycloalkyl radical is directly linked; and includes, but is not limited to, cyclopropylmethyl, cyclobutylmethyl, cyclopentylmethyl, 1-cyclopentylethyl, 2-cyclopentylethyl, cyclohexylmethyl, 1-cyclohexylethyl and 2-cyclohexylethyl. A similar use of the "alkyl" or "lower alkyl" terms is to be understood for aryl-alkyl-, aryl-lower alkyl- (eg. benzyl), -lower alkyl-alkenyl (eg. allyl), heteroaryl-alkyl-, and the like as used herein. For example, the term "aryl-alkyl-" means an alkyl radical, to which an aryl is bonded. Examples of aryl-alkyl-include, but are not limited to, benzyl(phenylmethyl), 1-phenylethyl, 2-phenylethyl and phenylpropyl.

As used herein, the term "heterocycle", either alone or in combination with another radical, means a monovalent radical derived by removal of a hydrogen from a three- to seven-membered saturated or unsaturated (including aromatic) heterocycle containing from one to four heteroatoms selected from nitrogen, oxygen and sulfur. Examples of such heterocycles include, but are not limited to, pyrrolidine, tetrahydrofuran, thiazolidine, pyrrole, thiophene, hydantoin, diazepine, imidazole, isoxazole, thiazole, tetrazole, piperidine, piperazine, homopiperidine, homopiperazine, 1,4-dioxane, 4-morpholine, 4-thiomorpholine, pyridine, pyridine-N-oxide or pyrimidine, and the like.

The term "alkenyl", as used herein, either alone or in combination with another radical, is intended to mean an unsaturated, acyclic straight chain radical containing two or more carbon atoms, at least two of which are bonded to each other by a double bond. Examples of such radicals include, but are not limited to, ethenyl(vinyl), 1-propenyl, 2-propenyl, and 1-butenyl.

The term "alkynyl", as used herein is intended to mean an unsaturated, acyclic straight chain radical containing two or more carbon atoms, at least two of which are bonded to each other by a triple bond. Examples of such radicals include, but are not limited to, ethynyl, 1-propynyl, 2-propynyl, and 1-butynyl.

The term "alkoxy" as used herein, either alone or in combination with another radical, means the radical —O—($C_{1-n}$)alkyl wherein alkyl is as defined above containing 1 or more carbon atoms, and includes for example methoxy, ethoxy, propoxy, 1-methylethoxy, butoxy and 1,1-dimethylethoxy. Where n is 1 to 6, the term "lower alkoxy" applies, as noted above, whereas the term "alkoxy" encompasses "lower alkoxy" as well as alkoxy groups where n is greater than 6 (for example, n=7 to 10). The term "aryloxy" as used herein alone or in combination with another radical means —O-aryl, wherein aryl is defined as noted above.

Typically, the structure of the multifunctional chemical agent is made up of Fn1, Fn2, and Fn3 (FIG. 10).

These methods are (a) linchpin directed modification (LDM) (FIG. 11); (b) protein directed protein modification (PDPM) (FIG. 12), and (c) Fn1 accelerated kinetic labeling by Fn2.

(a) Linchpin Directed Modification (LDM):

In LDM, Fn 1 reacts reversibly (or irreversibly) with rate of reaction $k_1$ and Fn 2 reacts irreversibly with rate of reaction $k_2$ in an intramolecular reaction. The multifunctional chemical agents are selected such that $k_1 \gg k_2$. The site for irreversible modification is controlled by combination of linker and chemo-selectivity of Fn1 and Fn2.

(b) Protein Directed Protein Modification (PDPM):

In PDPM, Fn 1 reacts reversibly (or irreversibly) with rate of reaction $k_1$ and Fn 2 reacts irreversibly with rate of reaction $k_2$ in an intermolecular reaction. The multifunctional chemical agents are selected such that $k_1 \gg k_2$. This process draws selectivity from restricted interaction between two proteins. In this technique, Fn1, Fn2 and linker are selected such as Fn2 has no choice but to react in intermolecular reaction.

PDPM offers a first method of its type to experimentally determine the surface of proteins involved in protein-protein interaction.

(c) Fn1 Accelerated Kinetic Labeling by Fn2

The key to success of this technique is a rapid and highly reversible reaction of Fn1 that plays the role of increasing the micro concentration of Fn2 near protein. Fn1 that would not react with N-terminus leads to site-selective modification of N-terminus. Fn1 that reacts with N-terminus leads to site-selective modification of most reactive backbone residue. The selection of residue depends on the choice of chemoselective Fn2. In a few cases, the chemoselectivity of Fn2 can be altered for labeling of N-terminus in a protein.

The method also allows the identification of the most reactive backbone residue among its multiple copies.

The combination of functional groups derives unique reactivity parameters from the protein that enables their site-selective modification.

In one embodiment, the multifunctional agents are selected from class 1, class 2, class 3, class 4, class 5, class 6 and class 7 reagents.

The selection of multifunctional agents is directed by the reactivity parameters from the protein for the selective modification.

Class 1: Site-selective Lys modification (A)

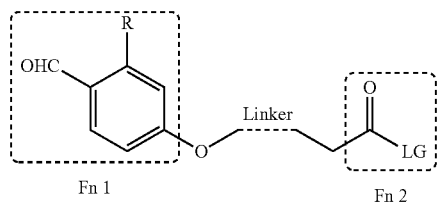

Fn 1: Reversible reaction with Lys
Fn 2: Irreversible reaction with Lys (B)

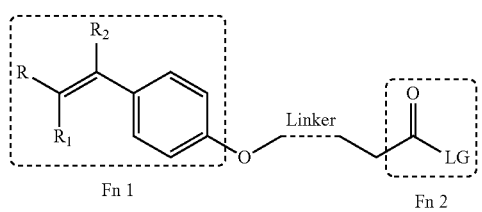

Fn 1: Reversible reaction with Cys
Fn 2: Irreversible reaction with Lys (C)

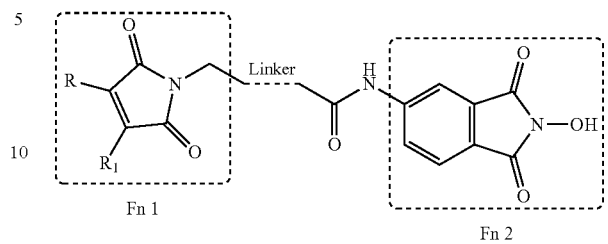

Fn 1: Reversible reaction with Cys
Fn 2: Irreversible reaction with Lys (D)

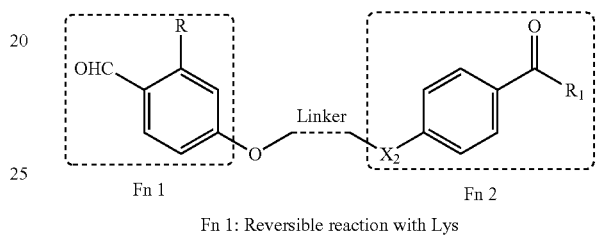

Fn 1: Reversible reaction with Lys
Fn 2: Irreversible reaction with Lys

Class 2: Site-selective His modification (A)

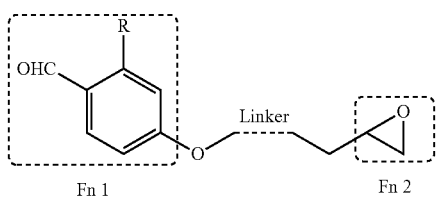

Fn 1: Reversible reaction with Lys
Fn 2: Irreversible reaction with His (B)

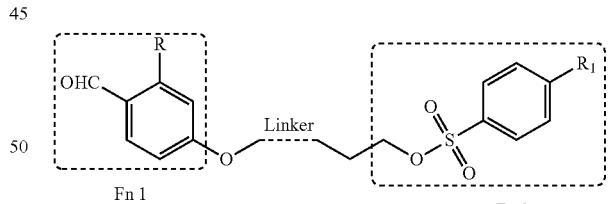

Fn 1: Reversible reaction with Lys
Fn 2: Irreversible reaction with His (C)

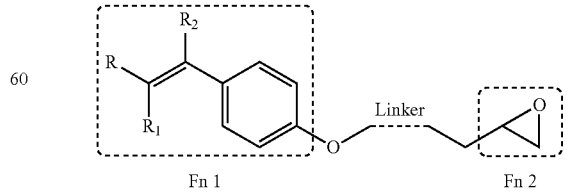

Fn 1: Reversible reaction with Cys
Fn 2: Irreversible reaction with His

Class 3: Site-selective Cys modification (A)

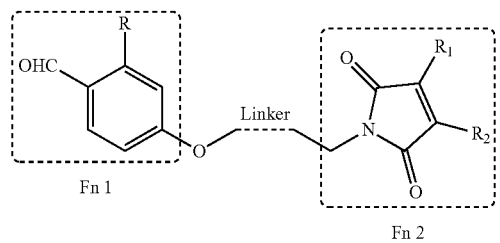

Fn 1: Reversible reaction with Lys
Fn 2: Irreversible reaction with Cys (B)

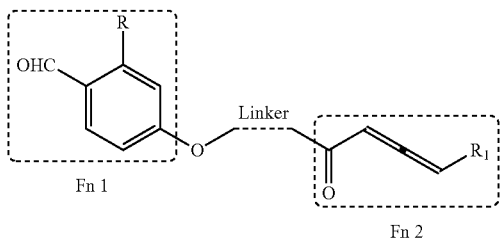

Fn 1: Reversible reaction with Lys
Fn 2: Irreversible reaction with Cys (C)

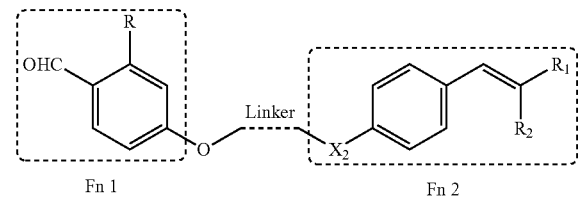

Fn 1: Reversible reaction with Lys
Fn 2: Irreversible reaction with Cys (D)

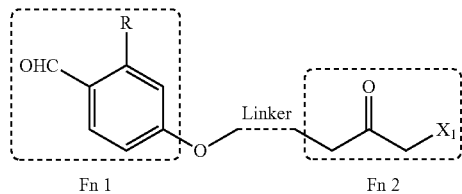

Fn 1: Reversible reaction with Lys
Fn 2: Irreversible reaction with Cys (E)

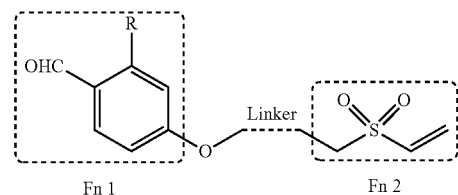

Fn 1: Reversible reaction with Lys
Fn 2: Irreversible reaction with Cys (F)

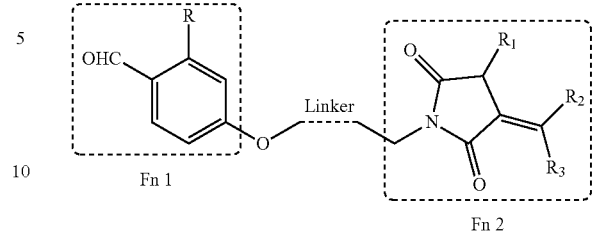

Fn 1: Reversible reaction with Lys
Fn 2: Irreversible reaction with Cys (G)

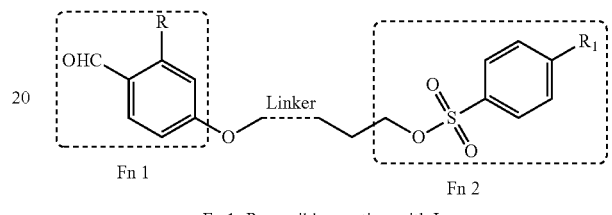

Fn 1: Reversible reaction with Lys
Fn 2: Irreversible reaction with Cys

Class 4: Site selective carboxylic acid (Asp or Glu) modification (A)

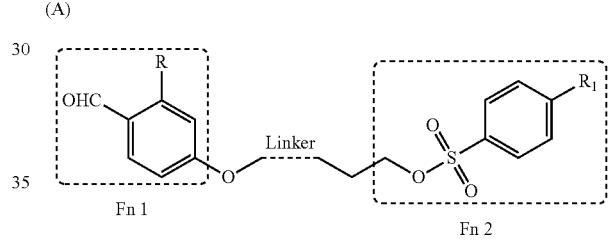

Fn 1: Reversible reaction with Lys
Fn 2: Irreversible reaction with His (B)

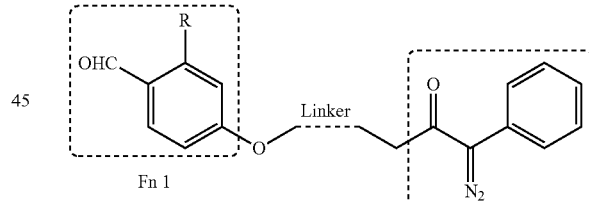

Fn 1: Reversible reaction with Lys
Fn 2: Irreversible reaction with Asp or Glu

Class 5: Site-selective Tyr modification

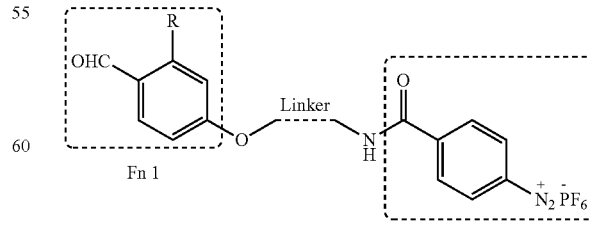

Fn 1: Reversible reaction with Lys
Fn 2: Irreversible reaction with Tyr

-continued

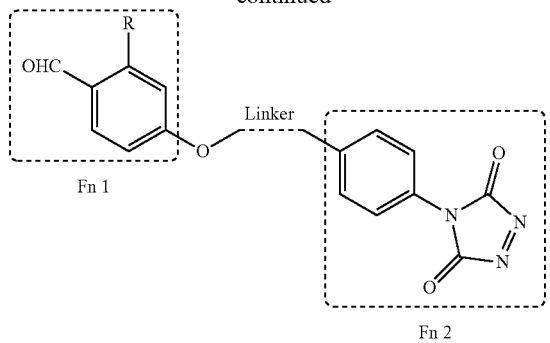

Fn 1: Reversible reaction with Lys
Fn 2: Irreversible reaction with Tyr

Class 6: Site-selective Arg modification

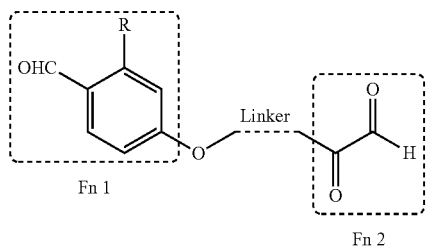

Fn 1: Reversible reaction with Lys
Fn 2: Irreversible reaction with Arg

Class 7: Site-selective Met modification

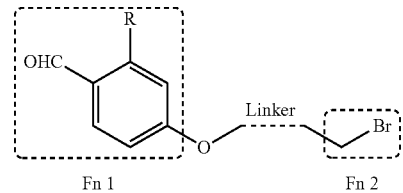

Fn 1: Reversible reaction with Lys
Fn 2: Irreversible reaction with Met

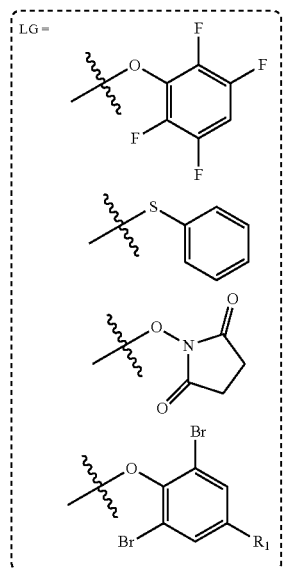

Procedures for synthesis of multifunctional chemical agents and characterization data are represented by class 2(A) agents and for the synthesis of the reagents of other classes, condensation of respective Fn1 and Fn2 using similar protocol and linkers are followed.

LDM reagents of class 2 (A) are selected from the group consisting of:

2-hydroxy-4-(oxiran-2-ylmethoxy)benzaldehyde (LDM Reagent 24)

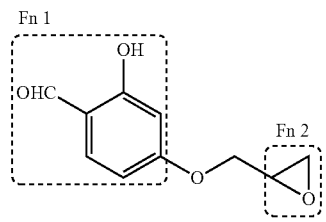 [SMILES: O=Cc1ccc(OCC2CO2)cc1O]

Oxiran-2-ylmethyl 2-(4-formyl-3-hydroxyphenoxy)acetate (LDM Reagent 29)

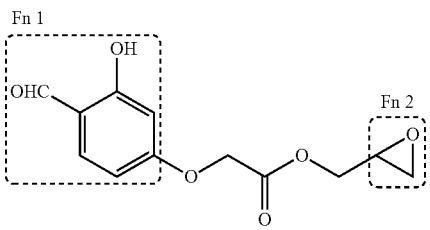 [SMILES: O=Cc1ccc(OCC(=O)OCC2CO2)cc1O]

Oxiran-2-ylmethyl 4-(4-formyl-3-hydroxyphenoxy)butanoate (LDM Reagent 2)

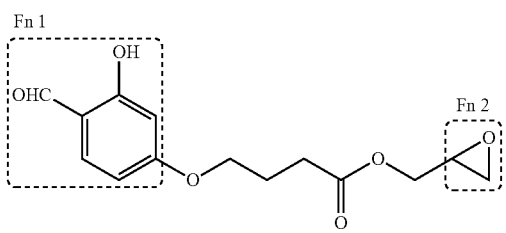 [SMILES: O=Cc1ccc(OCCCC(=O)OCC2CO2)cc1O]

17

Oxiran-2-ylmethyl 4-(4-(4-formyl-3-hydroxyphenoxy)butanamido)butanoate (LDM Reagent 36)

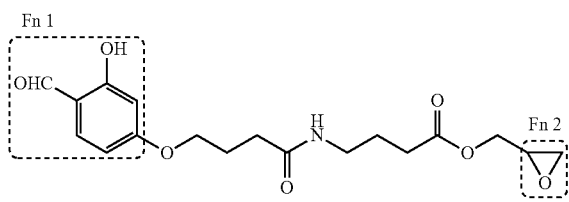 [SMILES: O=Cc1ccc(OCCCC(=O)NCCCC(=O)OCC2CO2)cc1O]

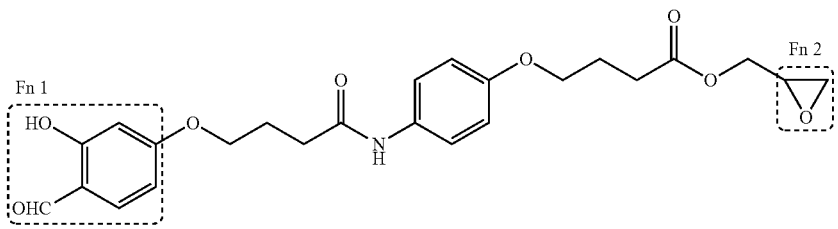 [SMILES: O=Cc1ccc(OCCCC(=O)Nc2ccc(OCCCC(=O)OCC3CO3)cc2)cc1O]

18

Oxiran-2-ylmethyl 4-(3-(4-(4-formyl-3 hydroxyphenoxy) butanamido) phenoxy) butanoate (LDM Reagent 9c)

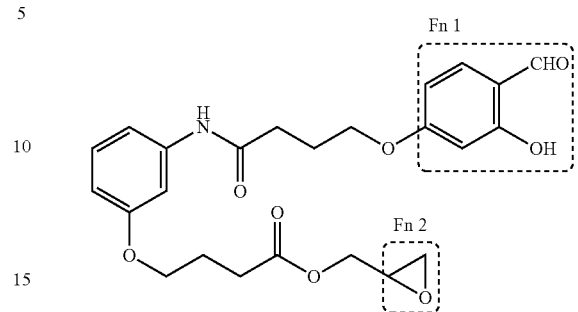

Oxiran-2-ylmethyl 4-(4-(4-(4-formyl-3-hdroxyphenoxy) butanamido) phenoxy) butanoate (LDM Reagent 20)

Oxiran-2-ylmethyl 4-(3-(2-(4-formyl-3-hydroxyphenoxy) acetamido) phenoxy) butanoate (LDM Reagent 9d)

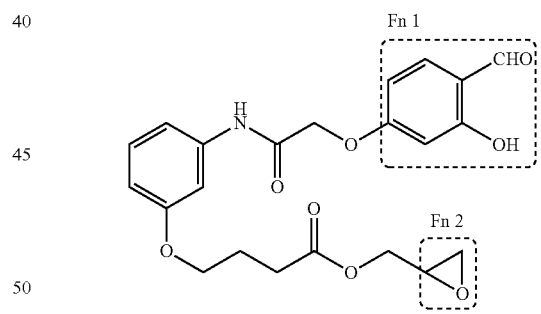

Oxiran-2-ylmethyl 4-(4-(2-(4-formyl-3-hydroxyphenoxy) acetamido) phenoxy) butanoate (LDM Reagent 9b)

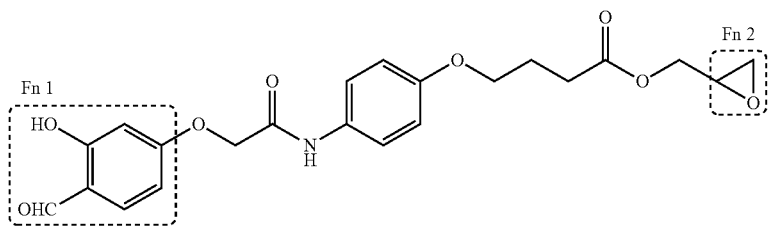 [SMILES: O=Cc1ccc(OCC(=O)Nc2ccc(OCCCC(=O)OCC3CO3)cc2)cc1O]

The site for modification of the proteins using the multifunctional chemical agents may be selected from the amino acids of the backbone (other than N-terminus) having reactive groups or hotspots.

The reactive amino acids for the site selective modification is selected from but not limited to Lysine, Histidine, Cysteine, Aspartic acid or Glutamic acid, Tyrosine, Arginine and Methionine of the native proteins or any functional biological molecules.

The rate of kinetics of reversible reaction Fn1 is $k_1$ and for Fn2 is $k_2$. The multifunctional chemical agents are selected such that $k_1 \gg k_2$.

A method for the site selective modification of proteins with the multifunctional chemical agents is a linchpin directed modification or protein directed modification or Fn1 accelerated kinetic labeling by Fn2.

The method of modification involves reaction for a single site labeling of proteins resulting in conjugation at backbone residue or N-terminus, late stage modification of proteins, dual site labeling of proteins, single site labeling in a mixture of proteins, protein-protein conjugation and protein cyclization.

The ratio of the protein to the LDM agent agent is 1:1 to 1:100. The reaction is carried out at a temperature 4-37° C. The reaction is carried at a pH 4-10.

The reaction is carried out for about 10 minutes to 72 hours. In the method of LDM reaction, Fn 1 reacts reversibly or irreversibly with rate of reaction $k_1$ and Fn 2 reacts irreversibly with rate of reaction $k_2$.

In the LDM reaction, the multifunctional chemical agents are selected such that the rate of reaction is $k_1 \gg k_2$.

The modified protein obtained by the method is reacted with hydroxylamine derivatives for an oxime product.

The hydroxylamine derivatives is selected from 3-(aminooxy)propyl 3,5-bis(trifluoromethyl)benzoate/3-(aminooxy)propyl 5-((3aS,4S,6aR)-2-oxohexahydro-1H-thieno[3,4-d]imidazol-4-yl)pentanoate/7-((3-(aminooxy)propyl)thio)-4-methyl-2H-chromen-2-one.

In the method the modified protein was reacted with sodium cyanoborohydride for the protein cyclization.

The modified protein from protein mixture was purified by using hydrazide-activated resin.

The native proteins or functional biological molecules for chemoselective modification is selected from RNase A, Lysozyme, Ubiquitin, Myoglobin, Cytochrome C, Chymotrypsinogen A, α-Lactalbumin, Aldolase etc.

The method of site selective modification of native proteins or any functional biological molecules using the multifunctional chemical agents are:

(i) Identifying the domain/residue to be modified with the multifunctional chemical agents;

(ii) Selecting the amino acid pair or a directing protein for reacting with the multifunctional chemical agents;

(iii) Selecting linker with appropriate length and geometry;

(iv) Reaction of protein and selected multifunctional chemical agent;

(v) Separation and purification of homogenously modified proteins.

ABBREVIATIONS AND ACRONYMS

DMAP 4-dimethylaminopyridine
DMSO Dimethyl sulfoxide
DMF N,N-Dimethyl formamide
DCM Dichloromethane
NEt$_3$ Triethylamine
Me Methyl
DIPEA N,N-Diisopropylethylamine
TFA Trifluoroacetic acid
DCC N,N'-Dicycloliexylcarbodiimide
EDC HCl 1-Ethyl-3-(3-dimethyl-aminopropyl)carbodiimide hydrochloride
MeOH Methanol
Δ Chemical shift
ESI Electro spray ionization
H Hour
HPLC High performance liquid chromatography
Mg Milligram
Min Minute
Ml Millilitre
Ml Microliter
Mmol Millimole
Mmol Micromole
Nmol Nanomole
Mp Melting point
NMR Nuclear magnetic resonance
Ppm Parts per million
$R_f$ Retention factor
TMS Tetramethylsilane
ToF Time of flight
M Molar
LCMS Liquid chromatography-mass spectrometry
HRMS High resolution-mass spectrometry
MALDI Matrix-Assisted Laser Desorption Ionization
TLC Thin-layer chromatography
UV Ultraviolet
MHz Megahertz
CD circular dichroism
Nm Nanometer
kDa Kilodaltons
MWCO Molecular weight cut-off

EXAMPLES

The following examples are for the purpose of illustration of the invention and are not intended in any way to limit the scope of the invention.

Example 1

General Procedures

The reagents, proteins, and enzymes were purchased from Sigma-Aldrich, Alfa Aeser and Merck Novabiochem. The organic solvents used were reagent grade. Aqueous buffers were prepared freshly using Millipore Grade I water (Resistivity>5 MΩ cm, Conductivity<0.2 μS/cm, TOC<30 ppb). Mettler Toledo (FE20) pH meter was used to adjust the final pH. The reaction mixture for the small molecules was stirred (Heidolph, 500-600 rpm). Proteins were either vortexed or incubated in incubator-shaker Thermo Scientific MaxQ 8000 (350 rpm, 25-37° C.). Cellulose membrane (MWCO, 6-8 kD) from Spectrum labs was used for dialysis. Amicon® Ultra-0.5 mL 3-kDa MWCO Centrifugal Filters from Merck Millipore was used to remove small molecules from protein mixture, desalting and buffer exchange. Organic solvents were removed by BUCHI rotavapor R-210/215 whereas aqueous samples were lyophilized by CHRiST ALPHA 2-4 LD plus lyophilizer. Circular Dichroism (CD) measurements were recorded on JASCO J-815 CD spectropolarimeter equipped with peltier temperature controller. All the spectra were measured with a scan speed of 50 nm/min, spectral band width 1 nm using 1 cm path length cuvette at 25° C.

Steady-state fluorescence spectra was carried out in HORIBA JOBIN YVON, FLUOROLOG 3-111. The fluorescence spectra were measured with a quartz cuvette of 1 mm path length.

Chromatography: Thin-layer chromatography (TLC) was performed on silica gel coated aluminium TLC plates (Merck, TLC Silica gel 60 F254). The compounds were visualized using a UV lamp (254 nm) and stains such as iodine, ninhydrin, 2,4-diphenylhydrazine. Where ever compounds were purified by chromatography, flash column chromatography was carried out on Combiflash Rf 200 or gravity columns using 230-400 or 100-200 mesh silica gel from Merck.

Nuclear magnetic resonance spectra: $^1$H, and $^{13}$CNMR spectra were recorded on Bruker Avance III 400 and 500 MHz NMR spectrometer. $^1$H NMR spectra were referenced to TMS (0 ppm) DMSO-$d_6$ (2.50 ppm) and acetone-$d_6$ (2.05 ppm) whereas $^{13}$C NMR spectra were referenced to CDCl$_3$ (77.16 ppm), DMSO-$d_6$ (39.52 ppm) and acetone-$d_6$ (29.84 ppm). Peak multiplicities are designated by the following abbreviations: s, singlet; bs, broad singlet; d, doublet; t, triplet; q, quartet; p, pentet; m, multiplet; dd, doublet of doublets, ddd, doublet of doublet of doublets. Spectra were recorded at 298 K.

Mass spectrometry: Agilent Technologies 1200 series HPLC paired to Agilent 6130 mass spectrometer (ESI/APCI) was used for LC-MS data. HPLC experiments of compounds were performed on Poroshell 300 SB-C18 column (2.1×75 mm×5 μm) with flow rate 0.4 ml/min. HRMS data were recorded on Bruker Daltonics MicroTOF-Q-II with electron spray ionization (ESI). Matrix assisted laser desorption/ionisation time of flight mass spectrometry was performed with Bruker Daltonics UltrafleXtreme Software-Flex control version 3.4, using sinapic acid and α-cyano-4-hydroxycinnamic acid (HCCA) matrix. Data analysis was performed using flex analysis. Peptide mass and fragment ion calculator Proteomics Toolkits were used for peptide mapping and sequencing of the protein.

Example 2

Procedures for Synthesis of Multifunctional Chemical Agents and Characterization Data Following reagents represent Class 2 (A). For the synthesis of the reagents of other classes, condensation of respective Fn1 and Fn2 using similar protocol and linkers are followed.

Example 2a

Synthesis of 2-hydroxy-4-(oxiran-2-ylmethoxy)benzaldehyde (24)

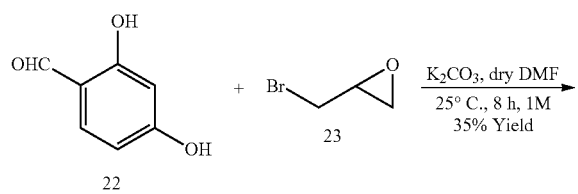

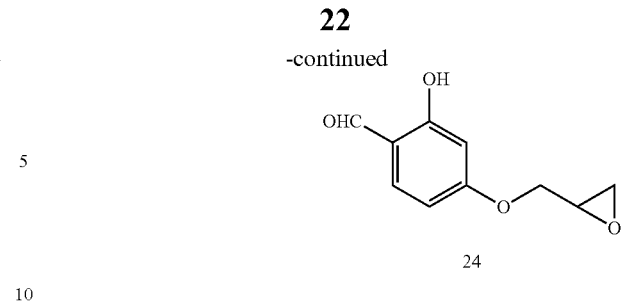

In 5 ml round bottom flask, 2,4-dihydroxybenzaldehyde (138 mg, 1 mmol) and K$_2$CO$_3$ (138 mg, 1 mmol) were dissolved in dry DMF (1 ml). To this solution, epibromohydrin (86 μl, 1 mmol) was added and stirred at room temperature. After 8 h, reaction mixture was carried out for ethylacetate:n-hexane (30:70) and water work up. The collected organic layers were dried with anh. sodium sulphate, filtered and concentrated in vacuo. The residue was purified by flash column chromatography using ethyl acetate:n-hexane (3:97) to give 24 (68 mg, 35% yield). $^1$H NMR (400 MHz, CDCl$_3$) δ 11.45 (s, 1H), 9.73 (s, 1H), 7.44 (d, J=8.7 Hz, 1H), 6.57 (dd, J=8.7, 2.3 Hz, 1H), 6.43 (d, J=2.2 Hz, 1H), 4.31 (dd, J=11.1, 2.9 Hz, 1H), 3.97 (dd, J=11.1, 5.9 Hz, 1H), 3.41-3.32 (m, 1H), 2.93 (t, J=4.5 Hz, 1H), 2.76 (dd, J=4.8, 2.6 Hz, 1H). $^{13}$C NMR (101 MHz, CDCl$_3$) δ 194.6, 165.6, 164.6, 135.5, 115.7, 108.8, 101.5, 69.2, 49.8, 44.7. HRMS (ESI) [MH]$^+$ calculated. C$_{10}$H$_{11}$O$_4$ 195.0657, found 195.0650.

Example 2b

Synthesis of oxiran-2-ylmethyl 2-(4-formyl-3-hydroxyphenoxy)acetate (29)

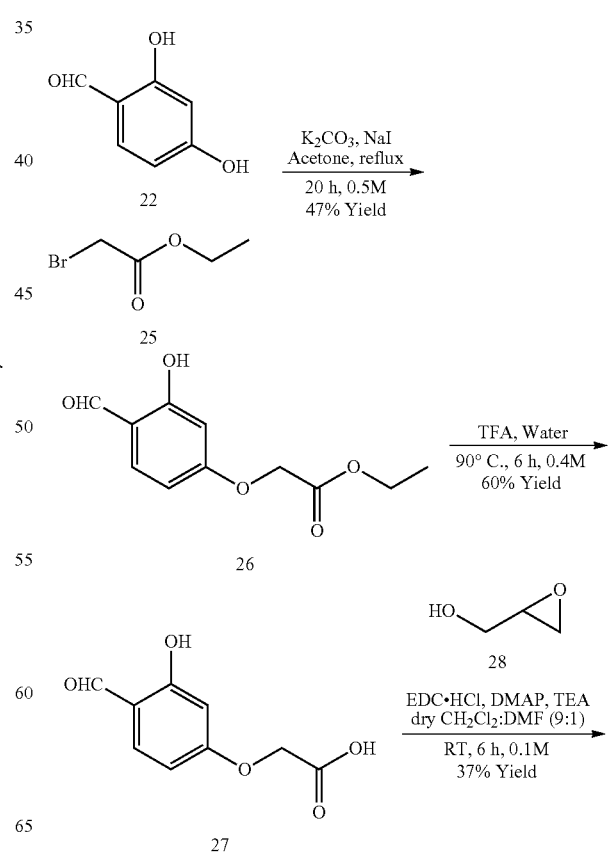

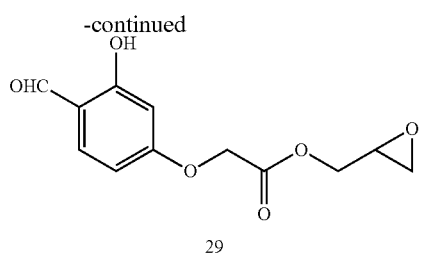

29

In a 10 ml round bottom flask, 2-(4-formyl-3-hydroxyphenoxy)acetic acid 27 (98 mg, 0.5 mmol), EDC.HCl (105 mg, 0.55 mmol), DMAP (18 mg, 0.15 mmol) and triethyl amine (140 μl, 1 mmol) were dissolved in dry CH$_2$Cl$_2$:DMF (5 ml, 9:1). To this solution, glycidol 28 (66 μl, 1 mmol) was added and stirred at room temperature for 6 h. The reaction mixture was concentrated in vacuo. The residue was purified by flash column chromatography using ethyl acetate:n-hexane (25:75) to give 29 (47 mg, 37% yield). $^1$H NMR (400 MHz, CDCl$_3$) δ 11.43 (s, 1H), 9.74 (s, 1H), 7.48 (d, J=8.7 Hz, 1H), 6.59 (dd, J=8.7, 2.4 Hz, 1H), 6.40 (d, J=2.3 Hz, 1H), 4.74 (s, 2H), 4.58 (dd, J=12.2, 2.9 Hz, 1H), 4.04 (dd, J=12.2, 6.4 Hz, 1H), 3.32-3.18 (m, 1H), 2.87 (t, J=4.5 Hz, 1H), 2.66 (dd, J=4.8, 2.6 Hz, 1H). $^{13}$C NMR (101 MHz, CDCl$_3$) δ 194.7, 167.7, 164.7, 164.4, 135.6, 116.0, 108.5, 101.7, 66.1, 65.0, 49.1, 44.7. HRMS (ESI) [MNa]$^+$ calculated. C$_{12}$H$_{12}$NaO$_6$ 275.0532, found 275.0528.

Example 2c

Synthesis of oxiran-2-ylmethyl 4-(4-formyl-3-hydroxyphenoxy)butanoate (2)

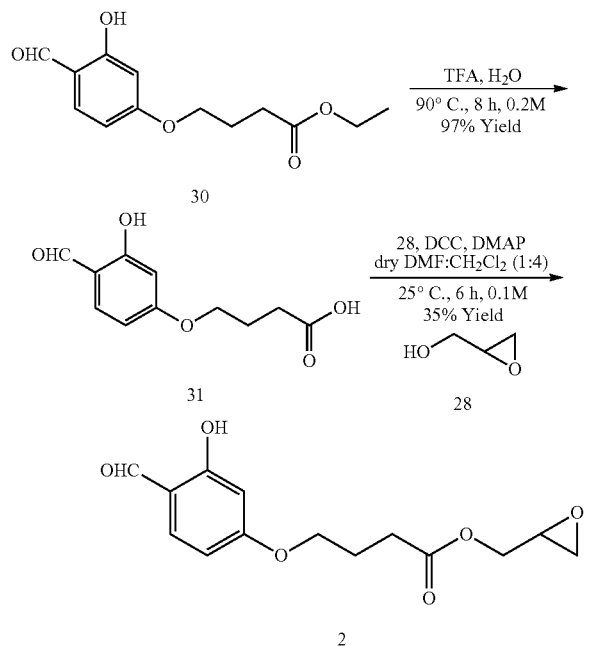

In a 25 ml round bottom flask, 4-(4-formyl-3-hydroxyphenoxy)butanoic acid (224 mg, 1 mmol), DCC (227 mg, 1.1 mmol) and DMAP (37 mg, 0.3 mmol) were dissolved in dry CH$_2$Cl$_2$:DMF (10 ml, 4:1). To this solution, glycidol (133 μl, 2 mmol) was added and stirred at room temperature for 6 h. The reaction mixture was filtered and filtrate was concentrated in vacuo. The residue was purified by flash column chromatography using ethyl acetate:n-hexane (20:80) to give 2 (98 mg, 35% yield). $^1$H NMR (400 MHz, CDCl$_3$) δ 11.45 (s, 1H), 9.71 (s, 1H), 7.43 (d, J=8.7 Hz, 1H), 6.53 (dd, J=8.7, 2.3 Hz, 1H), 6.41 (d, J=2.1 Hz, 1H), 4.45 (dd, J=12.3, 2.9 Hz, 1H), 4.08 (t, J=6.1, 2H), 3.94 (dd, J=12.3, 6.4 Hz, 1H), 3.27-3.16 (m, 1H), 2.85 (t, J=4.5 Hz, 1H), 2.65 (dd, J=4.8, 2.6 Hz, 1H), 2.58 (t, J=7.2 Hz, 2H), 2.24-2.09 (m, 2H). $^{13}$C NMR (101 MHz, CDCl$_3$) δ 194.5, 172.7, 166.1, 164.6, 135.4, 115.4, 108.7, 101.4, 67.3, 65.3, 49.4, 44.8, 30.5, 24.4. HRMS (ESI) [MNa]$^+$ calculated. C$_{14}$H$_{16}$NaO$_6$ 303.0845, found 303.0843.

Example 2d

Synthesis of oxiran-2-ylmethyl 4-(4-(4-formyl-3-hydroxyphenoxy)butanamido)butanoate (36)

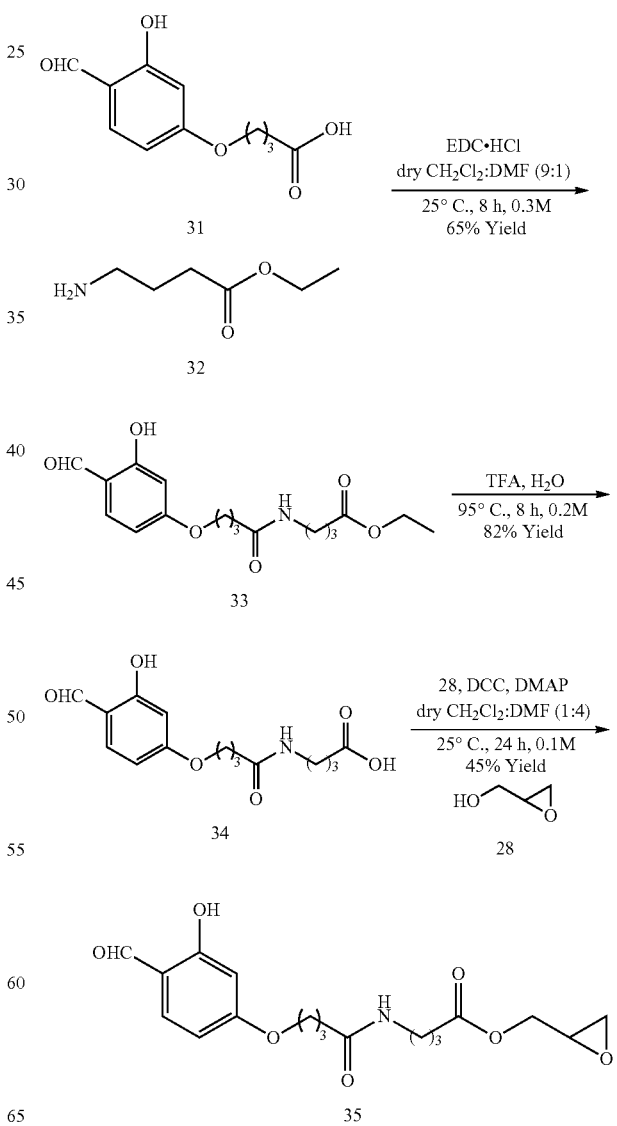

In a 25 ml round bottom flask, 4-(4-(4-formyl-3-hydroxyphenoxy)butanamido)butanoic acid (309 mg, 1 mmol), DCC (227 mg, 1.1 mmol) and DMAP (37 mg, 0.3 mmol) were dissolved in dry $CH_2Cl_2$:DMF (10 ml, 4:1). To this solution, glycidol 28 (133 μl, 2 mmol) was added and stirred at room temperature for 24 h. The reaction mixture was filtered and filtrate was concentrated in vacuo. The residue was purified by flash column chromatography using ethyl acetate:n-hexane (20:80) to give oxiran-2-ylmethyl 4-(4-(4-formyl-3-hydroxyphenoxy)butanamido)butanoate 36 (164 mg, 45% yield). $^1$H NMR (500 MHz, $CDCl_3$) δ 11.45 (s, 1H), 9.72 (s, J=9.3 Hz, 1H), 7.44 (d, J=8.7 Hz, 1H), 6.53 (dd, J=8.7, 2.3 Hz, 1H), 6.42 (d, J=2.2 Hz, 1H), 5.88 (s, 1H), 4.45 (dd, J=12.3, 2.9 Hz, 1H), 4.07 (t, J=6.0 Hz, 2H), 3.91 (dd, J=12.3, 6.4 Hz, 1H), 3.37-3.29 (m, 2H), 3.25-3.18 (m, 1H), 2.86 (t, J=4.5 Hz, 1H), 2.66 (dd, J=4.8, 2.6 Hz, 1H), 2.42 (t, J=7.2 Hz, 2H), 2.38 (t, J=7.2 Hz, 2H), 2.20-2.10 (m, 2H), 1.92-1.80 (m, 2H). $^{13}$C NMR (100 MHz, $CDCl_3$) δ 194.3, 173.0, 172.0, 166.0, 164.4, 135.3, 115.2, 108.4, 101.3, 67.5, 64.9, 49.2, 44.6, 38.9, 32.5, 31.5, 24.8, 24.6. HRMS (ESI) $[MNa]^+$ calculated. $C_{18}H_{23}NNaO_7$ 388.1372, found 388.1389.

Example 2e

Synthesis of oxiran-2-ylmethyl 4-(3-(4-(4-formyl-3 hydroxyphenoxy)butanamido)phenoxy)butanoate (9c)

In 25 ml round bottom flask, 4-(3-(4-(4-formyl-3-hydroxyphenoxy)butanamido)phenoxy)butanoic acid (200 mg, 0.5 mmol) was dissolved in ACN:DMF (1:1, 2.5 ml). To this solution, DIPEA (276 μl, 1.5 mmol) and epibromohydrin (128 μl, 1.5 mmol) were added and stirred at room temperature. The progress of the reaction was followed by thin layer chromatography. After 12 h, reaction mixture was quenched by 1N HCl (aq.) and compounds were extracted with ethyl acetate. The collected organic fractions were dried over anhydrous sodium sulfate, concentrated in vacuo. Purification of crude mixture by flash chromatography (MeOH:DCM, 1:99) gave oxiran-2-ylmethyl 4-(3-(4-(4-formyl-3-hydroxyphenoxy)butanamido)phenoxy)butanoate (80 mg, 35% yield). $^1$H NMR (500 MHz, $CDCl_3$) δ 11.46 (s, 1H), 9.73 (s, 1H), 7.44 (d, J=8.7 Hz, 1H), 7.32 (d, 2H), 7.20 (t, J=8.1 Hz, 1H), 6.98 (d, J=7.8 Hz, 1H), 6.66 (dd, J=8.1, 1.3 Hz, 1H), 6.54 (dd, J=8.6, 2.2 Hz, 1H), 6.43 (d, J=2.1 Hz, 1H), 4.45 (dd, J=12.3, 3.0 Hz, 1H), 4.13 (t, J=5.9 Hz, 2H), 4.02 (t, J=6.1 Hz, 2H), 3.95 (dd, J=12.3, 6.4 Hz, 1H), 3.23 (td, J=6.6, 2.9 Hz, 1H), 2.86 (t, J=4.5 Hz, 1H), 2.67 (dd, J=4.8, 2.6 Hz, 1H), 2.58 (t, J=7.3 Hz, 4H), 2.32-2.20 (m, 2H), 2.17-2.07 (m, 2H). $^{13}$C NMR (126 MHz, $CDCl_3$) δ 194.4, 172.9, 170.1, 166.0, 164.4, 159.3, 138.9, 135.3, 129.7, 115.3, 111.9, 110.7, 108.4, 106.0, 101.3, 67.4, 66.7, 65.0, 49.3, 44.7, 33.6, 30.5, 24.6, 24.5, 13.4. HRMS (ESI) $[MH]^+$ calculated. $C_{24}H_{28}NO_8$ 458.1815, found 458.1812.

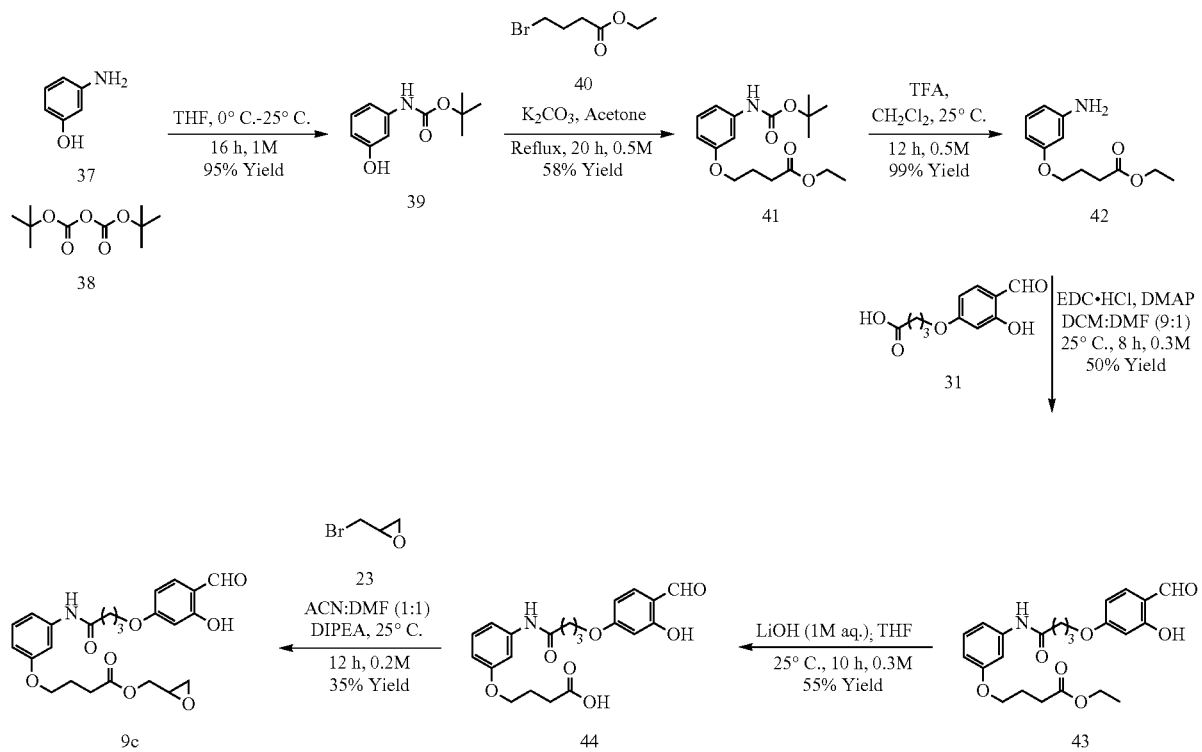

Example 2f

Synthesis of oxiran-2-ylmethyl 4-(4-(4-(4-formyl-3-hydroxyphenoxy)butanamido)phenoxy)butanoate (20)

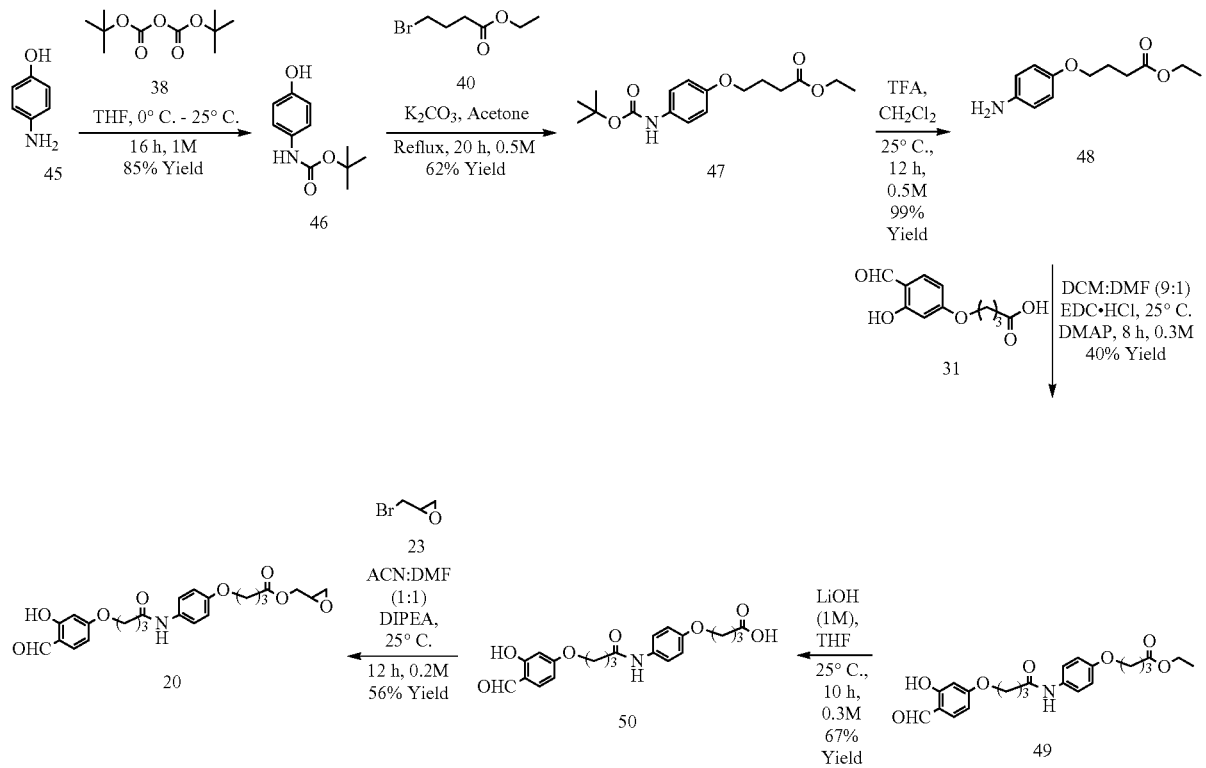

In 25 ml round bottom flask, 4-(4-(4-(4-formyl-3-hydroxyphenoxy)butanamido)phenoxy)butanoic acid (200 mg, 0.5 mmol) was dissolved in ACN:DMF (1:1, 2.5 ml). To this solution, DIPEA (276 μl, 1.5 mmol) and epibromohydrin (128 μl, 1.5 mmol) were added and stirred at room temperature. The progress of the reaction was followed by thin layer chromatography. After 12 h, reaction mixture was quenched by 1N HCl (aq.) and compounds were extracted with ethyl acetate. The collected organic fractions were dried over anhydrous sodium sulfate, concentrated in vacuo. Purification of crude mixture by flash chromatography (MeOH:DCM, 1:99) gave oxiran-2-ylmethyl 4-(4-(4-(4-formyl-3-hydroxyphenoxy)butanamido)phenoxy)butanoate 20 (128 mg, 56% yield). $^1$H NMR (500 MHz, CDCl$_3$) δ 11.45 (s, 1H), 9.71 (s, 1H), 7.42 (d, J=8.6 Hz, 1H), 7.37 (d, J=8.8 Hz, 2H), 7.15 (s, 1H), 6.83 (d, J=8.8 Hz, 2H), 6.53 (dd, J=8.6, 2.0 Hz, 1H), 6.42 (d, J=1.9 Hz, 1H), 4.43 (dd, J=12.3, 2.9 Hz, 1H), 4.12 (t, J=5.9 Hz, 2H), 3.99 (t, J=6.0 Hz, 2H), 3.94 (dd, J=12.3, 6.3 Hz, 1H), 3.20 (td, J=6.2, 3.0 Hz, 1H), 2.84 (t, J=4.5 Hz, 1H), 2.64 (dd, J=4.8, 2.6 Hz, 1H), 2.61-2.50 (m, 4H), 2.29-2.18 (m, 2H), 2.17-2.06 (m, 2H). $^{13}$C (126 MHz, CDCl$_3$) δ 194.3, 172.9, 169.9, 166.0, 164.4, 155.6, 135.3, 130.8, 121.7, 115.2, 114.8, 108.4, 101.3, 67.4, 66.8, 64.9, 49.3, 44.6, 33.4, 30.5, 24.7, 24.5. HRMS (ESI) [MH]$^+$ calculated. C$_{24}$H$_{28}$NO$_8$ 458.1815, found 458.1809.

Example 2g

Synthesis of oxiran-2-ylmethyl 4-(3-(2-(4-formyl-3-hydroxyphenoxy) acetamido) phenoxy) butanoate (9d)

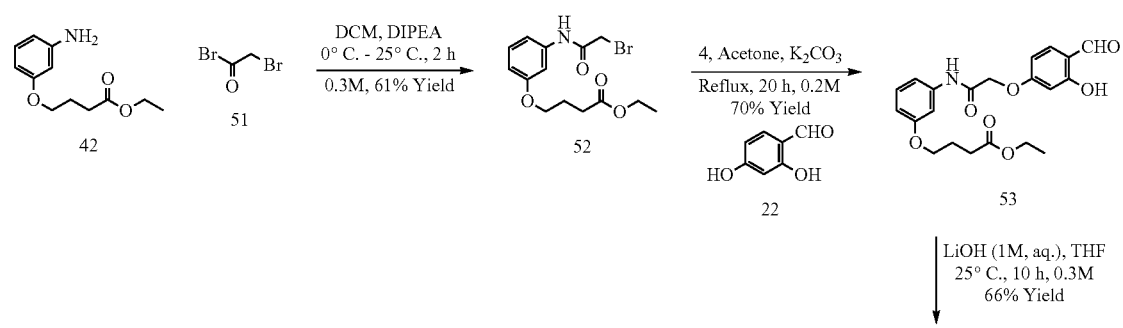

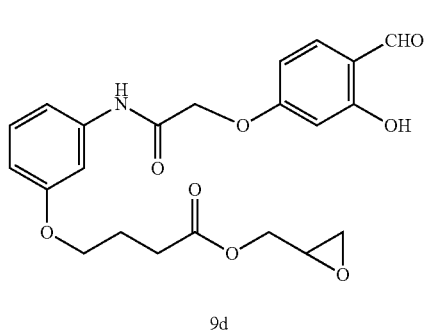

9d

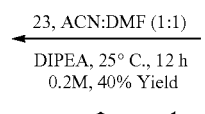

23, ACN:DMF (1:1)
DIPEA, 25° C., 12 h
0.2M, 40% Yield

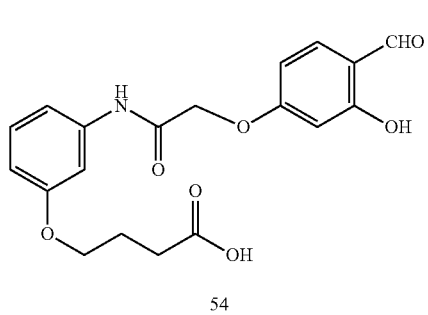

54

In 25 ml round bottom flask, 4-(3-(2-(4-formyl-3-hydroxyphenoxy)acetamido)phenoxy)butanoic acid (187 mg, 0.5 mmol) was dissolved in ACN:DMF (1:1, 2.5 ml). To this solution, DIPEA (276 μl, 1.5 mmol) and epibromohydrin (128 μl, 1.5 mmol) were added and stirred at room temperature. The progress of the reaction was followed by thin layer chromatography. After 12 h, reaction mixture was quenched by 1N HCl (aq.) and compounds were extracted with ethyl acetate. The collected organic fractions were dried over anhydrous sodium sulfate, concentrated in vacuo. Purification of crude mixture by flash chromatography (MeOH:DCM, 2:98) gave oxiran-2-ylmethyl 4-(3-(2-(4-formyl-3-hydroxyphenoxy) acetamido) phenoxy) butanoate 9d (86 mg, 40% yield). $^1$H NMR (500 MHz, CDCl$_3$) δ 11.43 (s, 1H), 9.78 (s, 1H), 8.12 (s, 1H), 7.54 (d, J=8.6 Hz, 1H), 7.29 (t, J=2.1 Hz, 1H), 7.24 (t, J=8.2 Hz, 1H), 7.07 (dd, J=8.0, 1.2 Hz, 1H), 6.70 (dd, J=8.3, 2.3 Hz, 1H), 6.66 (dd, J=8.6, 2.4 Hz, 1H), 6.54 (d, J=2.3 Hz, 1H), 4.65 (s, 2H), 4.44 (dd, J=12.3, 3.0 Hz, 1H), 4.03 (t, J=6.1 Hz, 2H), 3.94 (dd, J=12.3, 6.3 Hz, 1H), 3.26-3.18 (m, 1H), 2.87-2.82 (m, 1H), 2.65 (dd, J=4.9, 2.6 Hz, 1H), 2.58 (t, J=7.3 Hz, 2H), 2.19-2.08 (m, 2H). $^{13}$C NMR (126 MHz, CDCl$_3$) δ 194.6, 172.9, 164.8, 164.3, 163.5, 159.4, 137.7, 135.8, 129.9, 116.3, 112.4, 111.3, 107.8, 106.6, 102.4, 67.4, 66.7, 65.0, 49.3, 44.6, 30.5, 24.5. HRMS (ESI) [MH]$^+$ calcd. For C$_{22}$H$_{24}$NO$_8$ 430.1502, found 430.1489.

Example 2h

Synthesis of oxiran-2-ylmethyl 4-(4-(2-(4-formyl-3-hydroxyphenoxy) acetamido) phenoxy) butanoate (9b)

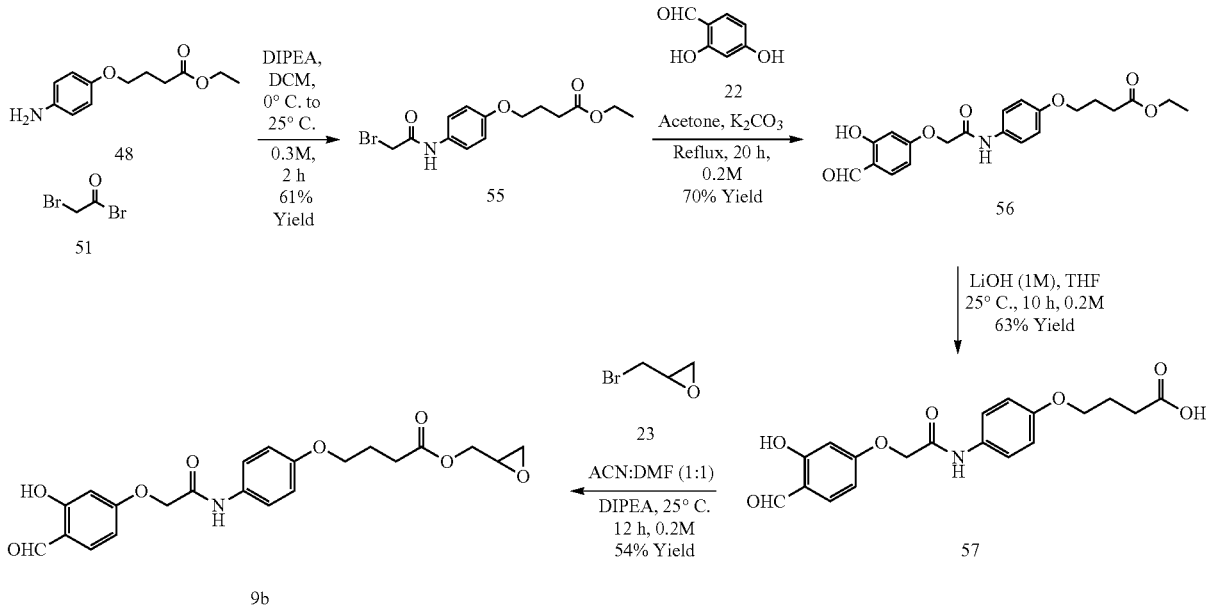

In 25 ml round bottom flask, 4-(4-(2-(4-formyl-3-hydroxyphenoxy)acetamido)phenoxy)butanoic acid (187 mg, 0.5 mmol) was dissolved in ACN:DMF (1:1, 2.5 ml). To this solution, DIPEA (276 μl, 1.5 mmol) and epibromohydrin (128 μl, 1.5 mmol) were added and stirred at room temperature. The progress of the reaction was followed by thin layer chromatography. After 12 h, reaction mixture was quenched by 1N HCl (aq.) and compounds were extracted with ethyl acetate. The collected organic fractions were dried over anhydrous sodium sulfate, concentrated in vacuo. Purification of crude mixture by flash chromatography (MeOH:DCM, 2:98) gave oxiran-2-ylmethyl 4-(4-(2-(4-formyl-3-hydroxyphenoxy) acetamido) phenoxy) butanoate 9b (116 mg, 54% yield). $^1$H NMR (500 MHz, CDCl$_3$) δ 11.43 (s, 1H), 9.78 (s, 1H), 8.06 (s, 1H), 7.53 (d, J=8.6 Hz, 1H), 7.50-7.43 (m, 2H), 6.91-6.84 (m, 2H), 6.65 (dd, J=8.6, 2.4 Hz, 1H), 6.53 (d, J=2.4 Hz, 1H), 4.64 (s, 2H), 4.44 (dd, J=12.3, 3.0 Hz, 1H), 4.00 (t, J=6.1 Hz, 2H), 3.94 (dd, J=12.3, 6.3 Hz, 1H), 3.21 (ddd, J=9.4, 4.1, 2.9 Hz, 1H), 2.84 (dd, J=4.8, 4.2 Hz, 1H), 2.64 (dd, J=4.9, 2.6 Hz, 1H), 2.58 (t, J=7.3 Hz, 2H), 2.18-2.08 (m, 2H). $^{13}$C NMR (126 MHz, CDCl$_3$) δ 194.6, 172.8, 164.7, 164.2, 163.5, 156.2, 135.8, 129.6, 122.1, 116.3, 114.9, 107.8, 102.3, 67.3, 66.8, 65.0, 49.3, 44.6, 30.5, 24.5. HRMS (ESI) [MH]$^+$ calculated. For C$_{22}$H$_{24}$NO$_8$ 430.1502, found 430.1517.

Example 3

Procedures for Protein Labeling, Late-Stage Modification, Single Site Single Protein Modification in a Protein Mixture, Protein Cyclization and Purification of Modified Protein from Protein Mixture General Procedure for Site-Selective Modification of Native Proteins (FIG. 4)

Protein (10 nmol) in phosphate buffer (140 μl, 0.1 M, pH 7.0) was taken in 1.5 ml Eppendorf tube. To this solution, LDM reagent (100 or 250 nmol) in DMSO (60 μl) from a freshly prepared stock solution was added and vortexed (350 rpm) at 25° C. The overall concentration of protein and LDM reagent was 50 μM and 500 μM or 1.25 mM respectively. After 12-30 h, the reaction mixture was diluted with acetonitrile:water (10:90, 1800 μl). Unreacted LDM reagent was removed by using Amicon® Ultra-0.5 mL 3-kDa MWCO centrifugal filters spin concentrator and the protein mixture was collected in aqueous media. The sample was analyzed by MALDI-ToF-MS or LCMS. The sample was exchanged into phosphate buffer (190 μl, 0.1 M, pH 7.0). To this solution, O-benzylhydroxylamine (5 μmol) in DMSO (10 μl) from a freshly prepared stock solution was added for late stage modification (oxime formation) and vortexed for 1-3 h. The excess of O-benzylhydroxylamine and salts were removed by using Amicon® Ultra-0.5 mL 3-kDa MWCO centrifugal filters spin concentrator. Modification of protein was analyzed by MALDI-ToF-MS or LCMS. The formation of the oxime product was 100% conversion. The aqueous sample was concentrated by lyophilization before subjecting it to digestion, peptide mapping and sequencing by MS-MS.

Example 4

Procedure for Installation of Various Tags on Myoglobin Through Late-Stage Modification (FIG. 5)

Myoglobin (10 nmol) in phosphate buffer (140 μl, 0.1 M, pH 7.0) was taken in 1.5 ml Eppendorf tube. To this solution, LDM reagent (250 nmol) in DMSO (60 μl) from a freshly prepared stock solution was added and vortexed (350 rpm) at 25° C. The overall concentration of protein and LDM reagent was 50 μM and 1.25 mM respectively. After 20 h, the reaction mixture was diluted with acetonitrile:phosphate buffer (10:90, 1800 μl). Unreacted LDM reagent was removed by using Amicon® Ultra-0.5 mL 3-kDa MWCO centrifugal filters spin concentrator. To the concentrated sample in phosphate buffer (160 μl, 0.1 M, pH 7.0), hydroxylamine derivatives such as 3-(aminooxy)propyl 3,5-bis(trifluoromethyl)benzoate/3-(aminooxy)propyl 5-((3aS,4S,6aR)-2-oxohexahydro-1H-thieno[3,4-d]imidazol-4-yl) pentanoate 7-((3-(aminooxy)propyl)thio)-4-methyl-2H-chromen-2-one (5 μmol) in DMSO (40 μl) from a freshly prepared stock solution was added to convert mono labeled Myoglobin into oxime product. The excess of O-hydroxylamine derivative and salts were removed by spin concentrator. The sample was analyzed by LCMS. The formation of the oxime product was 100% conversion. The Fluorine and coumarine derivative attached Myoglobin were carried for $^{19}$F NMR or Fluorescence analysis respectively. The salt free sample was concentrated by lyophilization before subjecting it to digestion, peptide mapping and sequencing by MS-MS.

Example 5

Procedure for Single Site Single Protein Modification in a Protein Mixture (FIG. 6)

Representative Mixture of Seven Proteins—Ubiquitin, Cytochrome C, RNase A, α-Lactalbumin, Lysozyme C, Myoglobin and Chymotrypsinogen A.

Each protein (10 nmol) in phosphate buffer (20 μl, 0.1 M, pH 7.0) were mixed in 2 ml eppendorf tube. To this solution, LDM reagent 20 (500 nmol) in DMSO (60 μl) from a freshly prepared stock solution was added and vortexed (350 rpm) at 25° C. After 24 h, the reaction mixture was diluted with acetonitrile:water (10:90, 1800 μl). Unreacted LDM reagent was removed by using Amicon® Ultra-0.5 mL 3-kDa MWCO centrifugal filters spin concentrator and the protein mixture was collected in the aqueous media.

The sample was transferred to phosphate buffer (190 μl, 0.1 M, pH 7.0) through buffer exchange. To this solution, O-benzylhydroxylamine (5 μmol) in DMSO (10 μl) from a freshly prepared stock solution was added for late stage modification (oxime formation) and vortexed for 1 h. The excess of O-benzylhydroxylamine and salts were removed by using Amicon® Ultra-0.5 mL 3-kDa MWCO centrifugal filters spin concentrator. Modification of protein was analyzed by MALDI-ToF-MS.

Example 6

Procedure for Protein Cyclization (FIG. 7)

Myoglobin (10 nmol) in phosphate buffer (350 μl, 0.1 M, pH 7.0) was taken in 1.5 ml Eppendorf tube. To this solution, LDM reagent (250 nmol) in DMSO (150 μl) from a freshly prepared stock solution was added and vortexed (350 rpm) at 25° C. The overall concentration of protein and LDM reagent was 50 μM and 1.25 mM respectively. After 20 h, the reaction mixture was diluted with acetonitrile:water (10:90, 1800 μl). Unreacted LDM reagent was removed by using Amicon® Ultra-0.5 mL 3-kDa MWCO centrifugal filters spin concentrator and the protein mixture was collected in aqueous media. The aldehyde group in the mono-labeled Myoglobin prefers the cyclized imine state as suggested by the LC-MS data. To convert this dynamic cyclized form into an irreversible state, NaCNBH$_3$ (200 μmol) in phosphate buffer (20 μl, pH 7.0) was added to the protein mixture (180 μl, pH 7.0) and incubated at 37° C. for 12 h. The sample was concentrated through spin concentrator (removal of excess NaCNBH$_3$, desalting) and analyzed by LC-MS. The salt free sample was concentrated by lyophilization before subjecting it to digestion, peptide mapping and sequencing by MS-MS.

Example 7

Procedure for Purification of Modified Protein from Protein Mixture Using Hydrazide-Activated Resin (FIG. 8)

Step 1. Preparation of Hydrazide-Sepharose® 4 Fast Flow

N-Hydroxysuccinimidyl-Sepharose® 4 Fast Flow isopropanol suspension (100 µl, 16-23 µmol per mL) was centrifuged in 2 ml Eppendorf tube at 400 rpm to remove the isopropanol. The beads were washed with phosphate buffer (3×1 ml, 0.1 M, pH 7.0) and suspended in the buffer (1 ml). To this solution, hydrazine mono hydrate (133 µg, 2.3 mmol, 80%) was added to allow end-over-end mixing for 12 h at 4° C. The suspension was centrifuged at 400 rpm to remove excess of the hydrazine mono hydrate, washed with phosphate buffer (3×1 ml, 0.1 M, pH 6.0) and suspended in the buffer (400 µl).

Step 2. Coupling of Hydrazide-Sepharose® 4 Fast Flow with Protein Mixture (Native Protein and Homogeneously Mono Labeled Protein)

Hydrazide-Sepharose® 4 Fast Flow suspension (100 µl) was taken in 2 ml Eppendorf tube. To this solution, protein mixture (7.5 nmol) in phosphate buffer (350 µl, 0.1 M, pH 6.0) and 1,4-Benzenediamine (81 µg, 750 nmol) in phosphate buffer (50 µl, 0.1 M, pH 6.0) were added and allowed to end-over-end mixing at 4° C. for 12 h. The suspension was centrifuged to collect unreacted protein, washed with phosphate buffer (3×1 ml, 0.1 M, pH 6.0) and suspended in buffer (480 µl).

Step 3. Collection of Oxime Product

O-benzylhydroxylamine (461 µg, 3.75 µmol) in DMSO (20 µl) from a freshly prepared stock solution was added to the solution and the suspension was allowed to end-over-end mixing at 4° C. for 3 h. The suspension was centrifuged to collect oxime product that is late stage modified mono labeled protein which was confirmed by LC-MS with no traces of native protein. The resin beads were washed with phosphate buffer (3×1 ml, 0.1 M, pH 6.0) and suspended in buffer (100 µl) for next batch purification. Various tags, $^{19}$F NMR, Fluorophore, PEGylation, Drugs etc. were installed on modified protein through oxime formation (step 3).

Example 8

Procedure for Protein Directed Protein Modification (PDPM) (Scheme 2)

Ubiquitin (50 µg, 5.8 nmol) in phosphate buffer (70 µl, pH 7.0) and Lysozyme C (83 µg, 5.8 nmol) in phosphate buffer (20 µl, pH 7.0) were mixed in 1.5 ml Eppendorf tube for 10 minutes. To this solution, S-phenyl 4-(4-formyl-3-hydroxyphenoxy)butanethioate (18.4 µg, 58 nmol) in DMSO (10 µl) from freshly prepared stock solution was added and vortexed at 25° C. After 72 h, the reaction mixture was diluted with acetonitrile:water (10:90, 900 µl). The unreacted PDPM reagent was removed by using Amicon® Ultra-0.5 mL 3-kDa MWCO centrifugal filters spin concentrator and the protein mixture was collected in aqueous media. The sample was analyzed by MALDI-ToF-MS using sinapic acid as matrix. The sample was concentrated by lyophilization before subjecting it to digestion, peptide mapping and sequencing by MS-MS.

Advantages:

Single-site chemical modification of native proteins or un-engineered proteins.

Chemoselective and site-selective chemical modification of native proteins or un-engineered proteins.

The technique offers predictability and diversity in site-selective protein modification of native proteins.

The technique offers opportunity for late stage modification of labeled site.

A simple protocol was developed for the purification of modified protein from protein mixture using hydrazide-activated resin The derivatives of native proteins thus obtained by site selective modification has wide range of applications in probing biological interactions, ligand discovery, disease diagnosis, and high-throughput screening.

Directed therapeutics is typically achieved by conjugating polymer chains, glycosylation, chromophores, and biohybrid materials. Obtaining homogenous protein-protein conjugates.

REFERENCES

Usera; Aimee et al 2015, US Patent 20150017192. (Site-specific chemoenzymatic protein modifications)

Hober; Sophia et al 2013, US Patent 20130184442. Method for labeling of compounds) Schultz et al 2012, US Patent 20120202243. (In vivo incorporation of unnatural amino acids)

Schultz et al 2015, US Patent 20150018523. (Unnatural reactive amino acid genetic code additions)

Davis et al 2011, US Patent 20110059501. (Protein glycosylation)

Noren, C. J.; Anthony-Cahill, S. J.; Griffith, M. C.; Schultz, P. G. *Science,* 1989, 244, 182-188. (A General Method for Site-Specific Incorporation of Unnatural Amino Acids into Proteins)

Cornish, V. W.; Benson, D. R.; Altenbach, C. A. Hideg, K.; Hubbell, W. L.; Schultz, P. G. *Proc. Natl. Acad. Sci. (USA),* 1994, 91, 2910-2914. (Site Specific Incorporation of Biophysical Probes into Proteins)

Kim, C.; Axup, J.; Schultz, P. G. *Curr. Opin. Chem. Biol.* 2013, 17, 412-419. Protein conjugation with genetically encoded unnatural amino acids)

Xiao, H.; Chatterjee, A.; Choi, S.; Bajjuri, K. M.; Sinha, S. C.; Schultz, P. G.; *Angew. Chem. Int. Ed.* 2013, 52, 14080-14083. (Genetic incorporation of multiple unnatural amino acids into proteins into mammalian cells)

Chalker, J. M.; Bernardes, G. J. L.; Davis, B. G. *Acc. Chem. Res.,* 2011, 44, 730-741. (A "Tag-and-Modify" Approach to Site-Selective Protein Modification)

Krueger, A. T.; Imperiali, B. *ChemBioChem* 2013, 14, 788-799. (Fluorescent Amino Acids: Modular Building Blocks for the Assembly of New Tools for Chemical Biology) Smith, E. L.; Giddens, J. P.; Iavarone, A. T.; Godula, K.; Wang, L. X.; Bertozzi, C. R. *Bioconjug. Chem.* 2014, 25,788-795. (Chemoenzymatic Fc Glycosylation via Engineered Aldehyde Tags.

The invention claimed is:

1. A method for the site selective modification of a protein with a multifunctional chemical agent, comprising the following steps:
   (i) identifying a domain/residue to be modified with the multifunctional chemical agent;
   (ii) selecting an amino acid pair or a directing protein for reacting with the multifunctional chemical agent;
   (iii) selecting a linker;
   (iv) reacting the protein and the selected multifunctional chemical agent; and (v) separating and purifying a homogenously modified protein,
the multifunctional chemical agent further comprising functional agents Fn1 and Fn2 and a linker to connect Fn1 and Fn2 and an affinity tag or purification tag Fn3;
Fn 1 is selected from
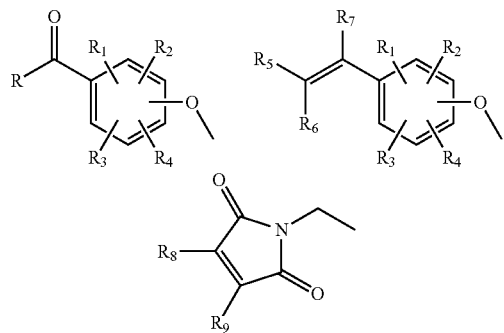
Fn 2 is selected from
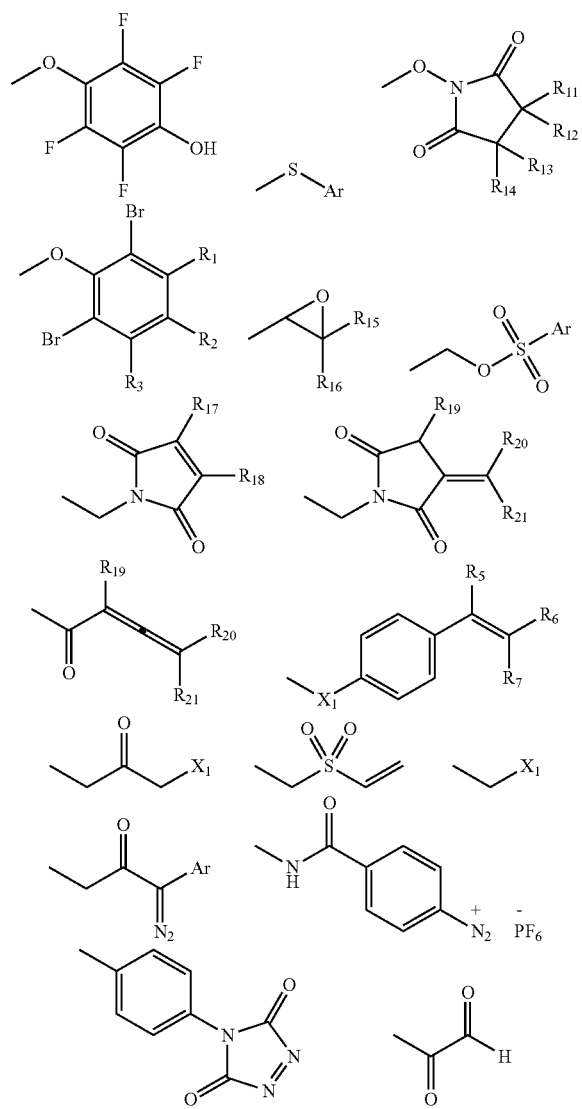
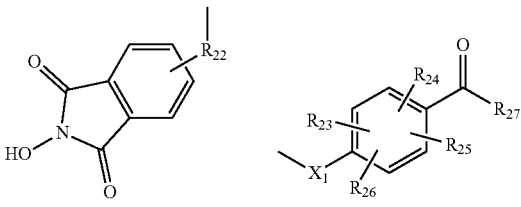
Ar = Aryl group; $X_1$ = halide, leaving group or heteroatom
Linkers are selected from
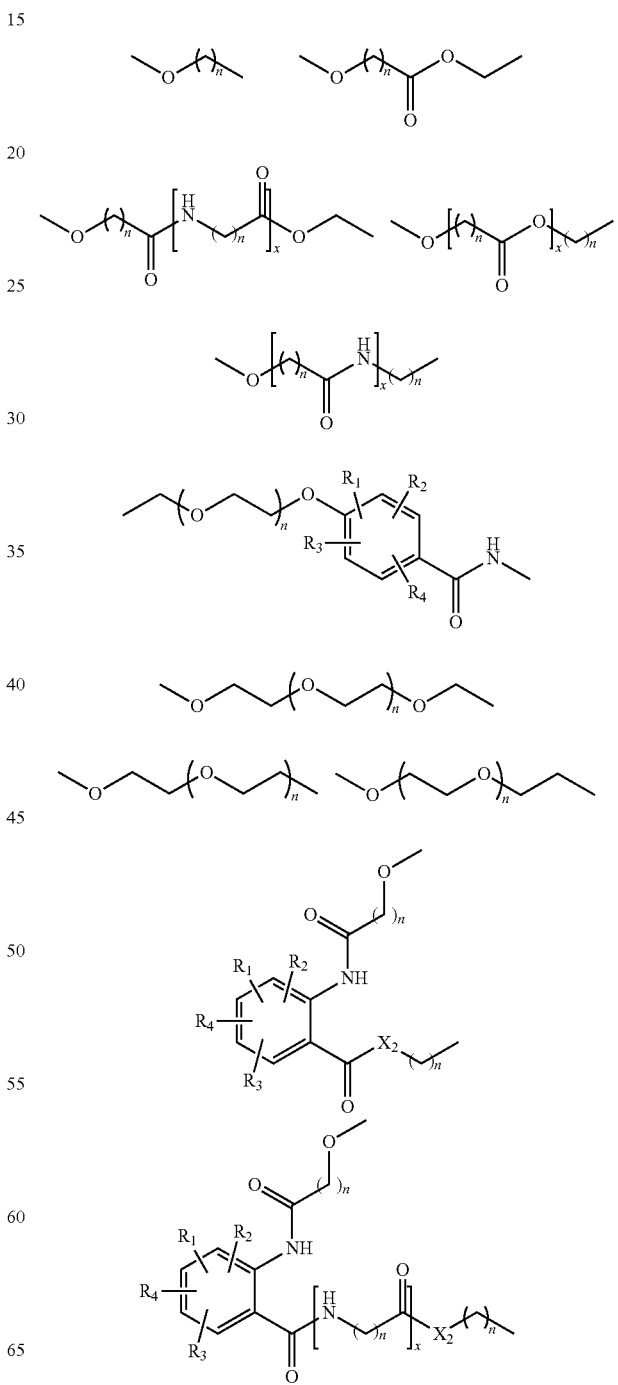

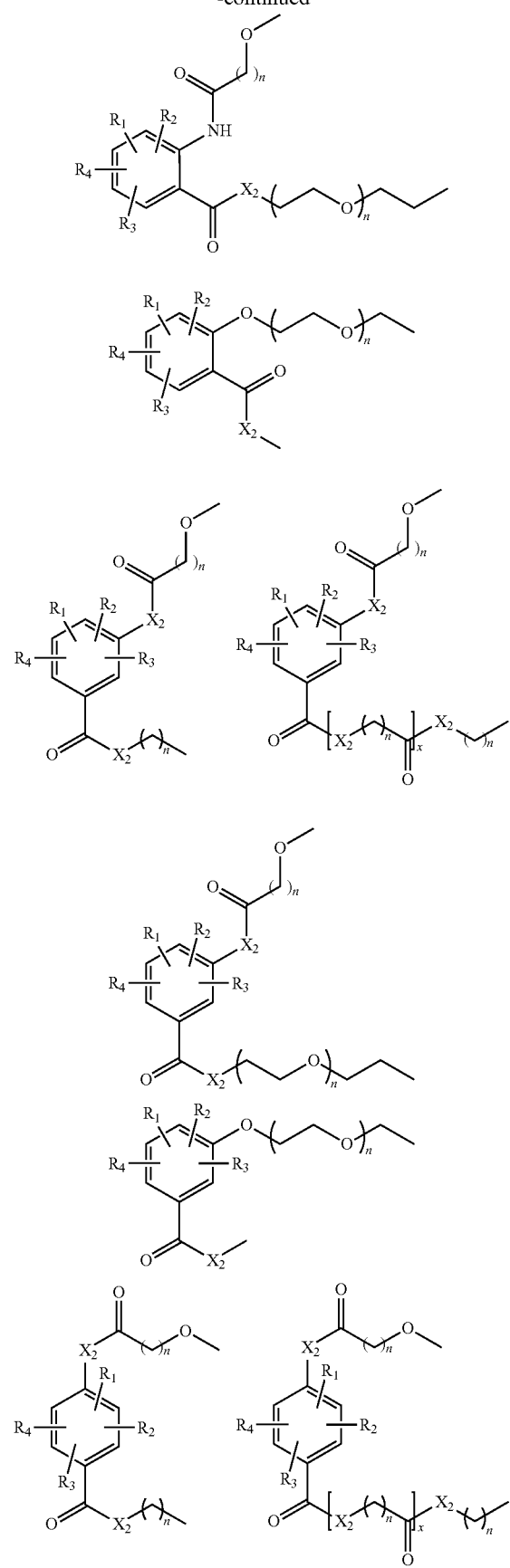
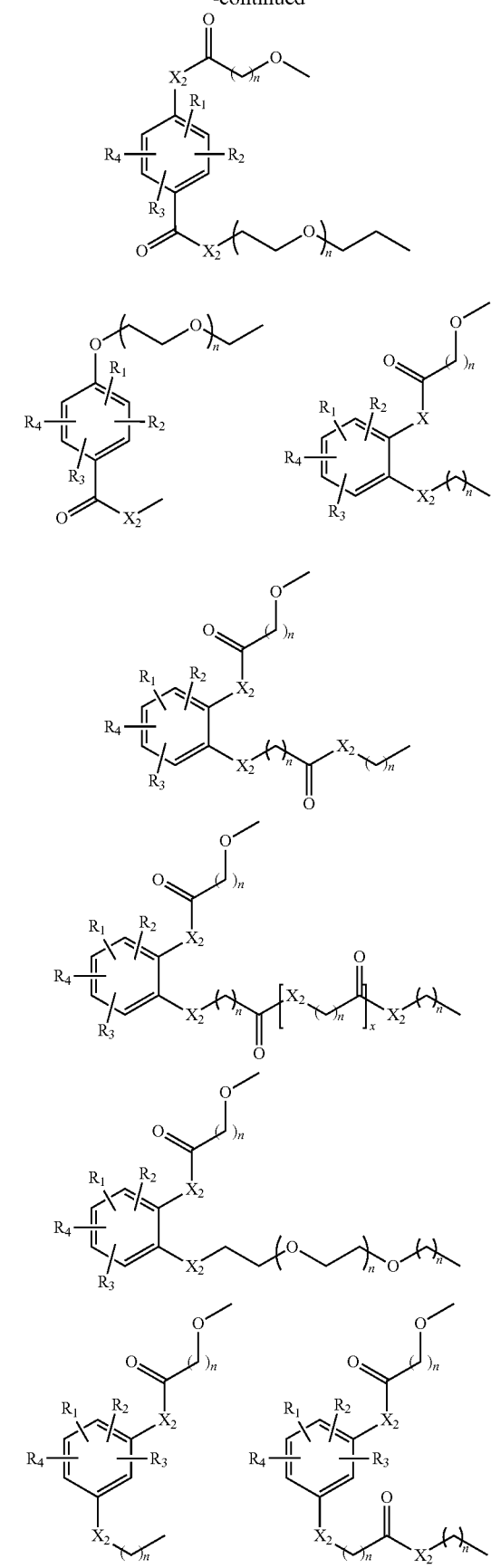

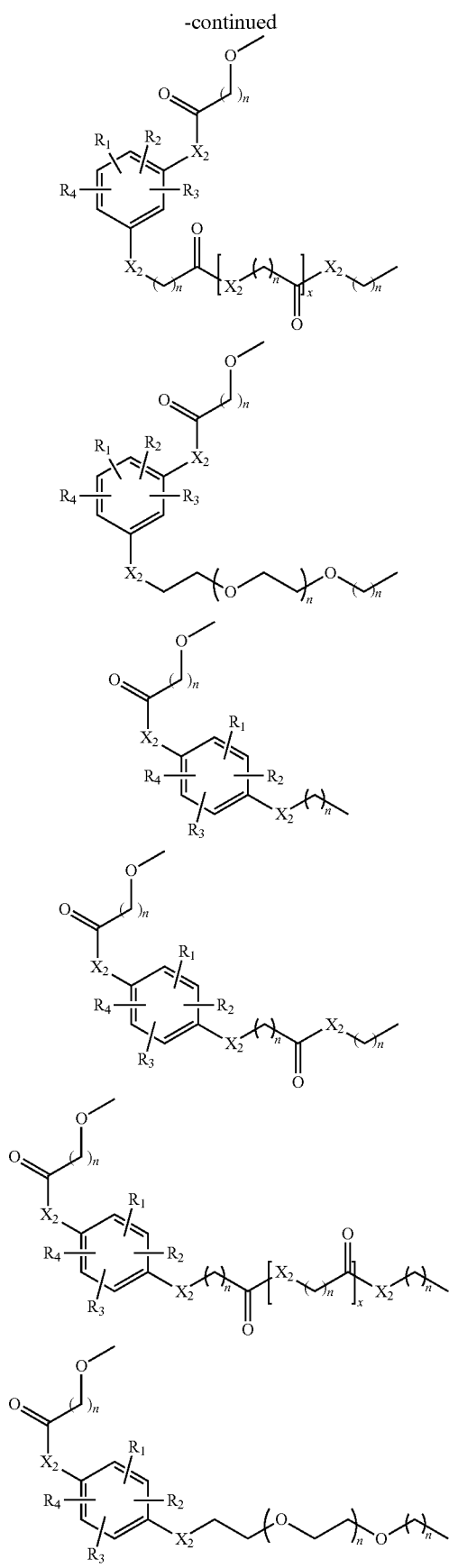

wherein
$X_2$=O or NH,
n=1-10,
x=1-10,
R is independently selected from H; alkyl; cycloalkyl; aryl,
$R_1$, $R_2$, $R_3$ and $R_4$ are independently selected from H; hydroxyl; —B(OR$^{1*}$)(OR$^{1**}$)
  wherein R$^{1*}$ and R$^{1**}$ are independently selected from H; alkyl; lower alkyl; cycloalkyl; aryl; heteroaryl; alkenyl; heterocycle; halides; nitro; —C(O)OR$^{2*}$
    wherein R$^{2*}$ is selected from H, alkyl, cycloalkyl and aryl; —C(O)NR$^{3}$R$^{3*}$,
      wherein R$^{3}$ and R$^{3*}$ are independently selected from H, alkyl; cycloalkyl and aryl; —CH$_2$C(O)R$_a$,
      wherein R$_a$ is selected from —OH, lower alkyl, cycloalkyl; aryl, -lower alkyl-aryl, -cycloalkyl-aryl; or —NR$_b$R$_c$,
      where R$_b$ and R$_c$ are independently selected from H, lower alkyl, cycloalkyl; aryl or -lower alkyl-aryl; —C(O)R$_d$,
      wherein R$_d$ is selected from lower alkyl, cycloalkyl; aryl or -lower alkyl-aryl; or -lower alkyl-OR$_e$,
      wherein R$_e$ is a suitable protecting group or OH group,
$R_5$, $R_6$, and $R_7$ are independently selected from H; nitro; cyano; halides; alkyl; cycloalkyl; aryl and C(O)OR$^{4*}$,
  wherein R$^{4*}$ is selected from H, alkyl; cycloalkyl and aryl; —C(O)NR$^{5}$R$^{5*}$,
    wherein R$^{5}$ and R$^{5*}$ are independently selected from H, alkyl; cycloalkyl and aryl,
$R_8$ and $R_9$ are independently selected from H; halides; alkyl; cycloalkyl and aryl,
$R_{10}$ is selected from H; nitro; cyano; halides; alkyl; cycloalkyl; aryl and C(O)OR$^{6*}$,
  wherein R$^{6*}$ is selected from H, alkyl; cycloalkyl and aryl; —C(O)NR$^{7}$R$^{7*}$,
    wherein R$^{7}$ and R$^{7*}$ are independently selected from H, alkyl; cycloalkyl and aryl,
$R_{11}$, $R_{12}$, $R_{13}$ and $R_{14}$ are independently selected from H; alkyl; cycloalkyl, aryl and —SO$_3$R$^{8*}$,
  wherein R$^{8*}$ is selected from H; Na,
$R_{15}$ and $R_{16}$ are independently selected from H; alkyl; cycloalkyl; aryl and C(O)OR$^{9*}$
  wherein R$^{9*}$ is selected from H, alkyl; cycloalkyl and aryl; —C(O)NR$^{10}$R$^{10*}$,
    wherein R$^{10}$ and R$^{10*}$ are independently selected from H, alkyl; cycloalkyl and aryl,
$R_{17}$ and $R_{18}$ are independently selected from H; halides; alkyl; cycloalkyl and aryl,
$R_{19}$, $R_{20}$, and $R_{21}$ are independently selected from H; alkyl; aryl and C(O)OR$^{11*}$,
  wherein R$^{11*}$ is selected from H, alkyl; cycloalkyl and aryl; —C(O)NR$^{12}$R$^{12*}$,
    wherein R$^{12}$ and R$^{12*}$ are independently selected from H, alkyl; cycloalkyl and aryl,
$R_{22}$ is selected from alkyl; cycloalkyl; aryl; —NR$^{13*}$R$^{13**}$,
  wherein R$^{13*}$ and R$^{13}$ are independently selected from H, alkyl; cycloalkyl; aryl and —COR$^{14*}$,
    wherein R$^{14***}$ is alkyl; cycloalkyl and aryl,
$R_{23}$, $R_{24}$, $R_{25}$, $R_{26}$ and $R_{27}$ are selected from H; alkyl; lower alkyl; cycloalkyl; aryl; heteroaryl; alkenyl; heterocycle; halides; OR$^{15*}$,
  wherein R$^{15*}$ is selected from H, alkyl; cycloalkyl and aryl, wherein the modification is a linchpin directed modification or protein directed modification or Fn1 accelerated kinetic labeling by Fn2, and wherein the protein obtained by the method is reacted with a hydroxylamine derivative to form an oxime product.

2. The method as claimed in claim 1, wherein the ratio of the protein to the multifunctional agent is 1:1 to 1:100.

3. The method as claimed in claim 1, wherein the method is carried out at a temperature 4-37° C.

4. The method as claimed in claim 1, wherein the method is carried at a pH 4-10.

5. The method as claimed in claim 1, wherein the method is carried out for 10 minutes to 72 hours.

6. The method as claimed in claim 1, wherein the hydroxylamine derivative is selected from 3-(aminooxy)propyl 3,5-bis(trifluoromethyl)benzoate, 3-(aminooxy)propyl 5-((3aS,4S,6aR)-2-oxohexahydro-1H-thieno[3,4-d]imidazol-4-yl)pentanoate or 7-((3-(aminooxy)propyl)thio)-4-methyl-2H-chromen-2-one.

7. The method as claimed in claim 1, wherein the modified protein is further purified from the protein mixture by using a hydrazide-activated resin.

8. The method as claimed in claim 1, wherein in the multifunctional chemical agent, Fn1 reacts reversibly or irreversibly with a rate of reaction $k_1$ and Fn2 reacts irreversibly with a rate of reaction $k_2$ in an intramolecular reaction, wherein Fn1 and Fn2 are selected such that the rate of reaction is $k_1 \gg k_2$, and wherein the method is for a single site labeling of the protein resulting in one or more of conjugation at a backbone residue or N-terminus, late stage modification of the protein, dual site labeling of the protein, single site labeling in a mixture of proteins, protein-protein conjugation and protein cyclization.

9. The method as claimed in claim 8, wherein the site for selective modification of the protein is selected from Lysine, Histidine, Cysteine, Aspartic acid or Glutamic acid, Tyrosine, Arginine and Methionine of the native protein or any functional biological molecule, wherein Fn1 reacts with either Lysine or Cystine, and wherein Fn2 reacts with Lysine, Histidine, Cysteine, Aspartic acid, Glutamic acid, Tyrosine, Arginine or Methionine.

10. A method for the site selective modification of a protein with a multifunctional chemical agent, comprising the following steps:

(i) identifying a domain/residue to be modified with the multifunctional chemical agent;

(ii) selecting an amino acid pair or a directing protein for reacting with the multifunctional chemical agent;

(iii) selecting a linker;

(iv) reacting the protein and the selected multifunctional chemical agent; and (v) separating and purifying a homogenously modified protein, the multifunctional chemical agent further comprising functional agents Fn1 and Fn2 and a linker to connect Fn1 and Fn2 and an affinity tag or purification tag Fn3;

Fn 1 is selected from

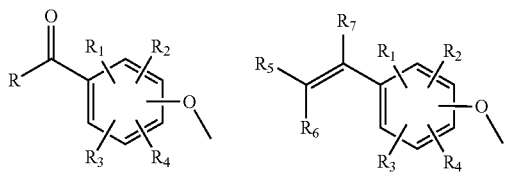

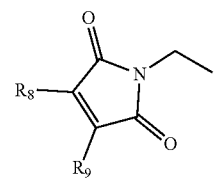

Fn 2 is selected from

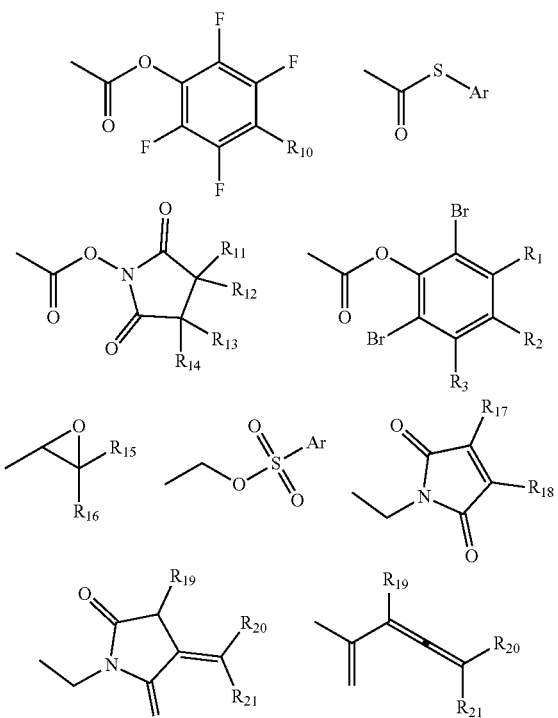

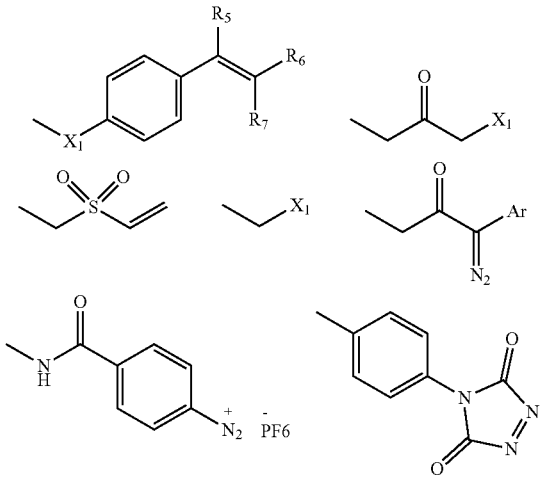

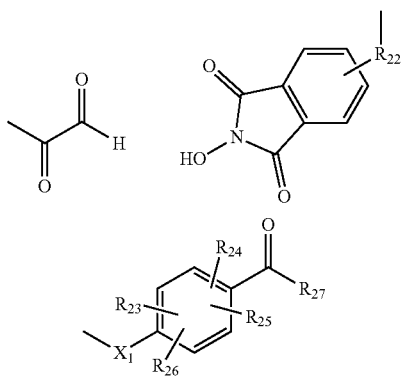
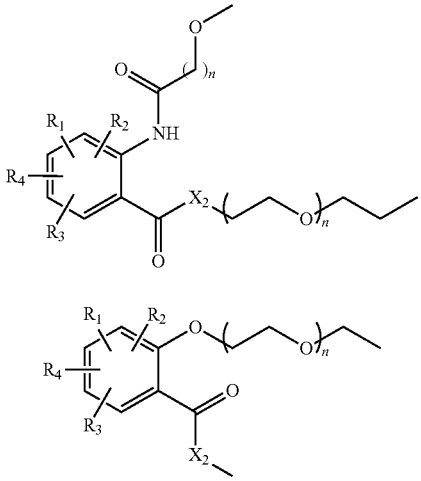
Ar=Aryl group; $X_1$=halide, leaving group or heteroatom
Linkers are selected from
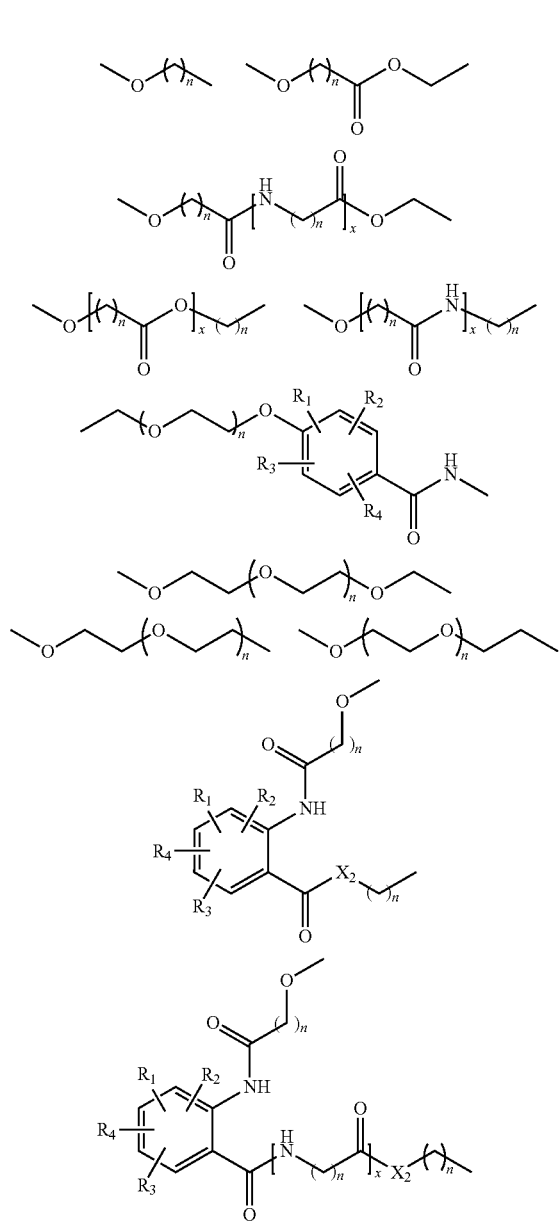
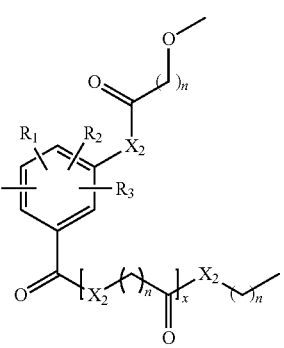
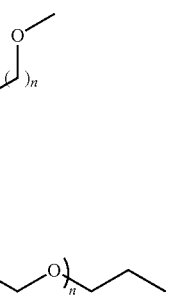
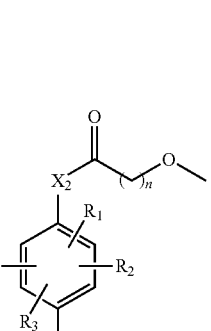

-continued
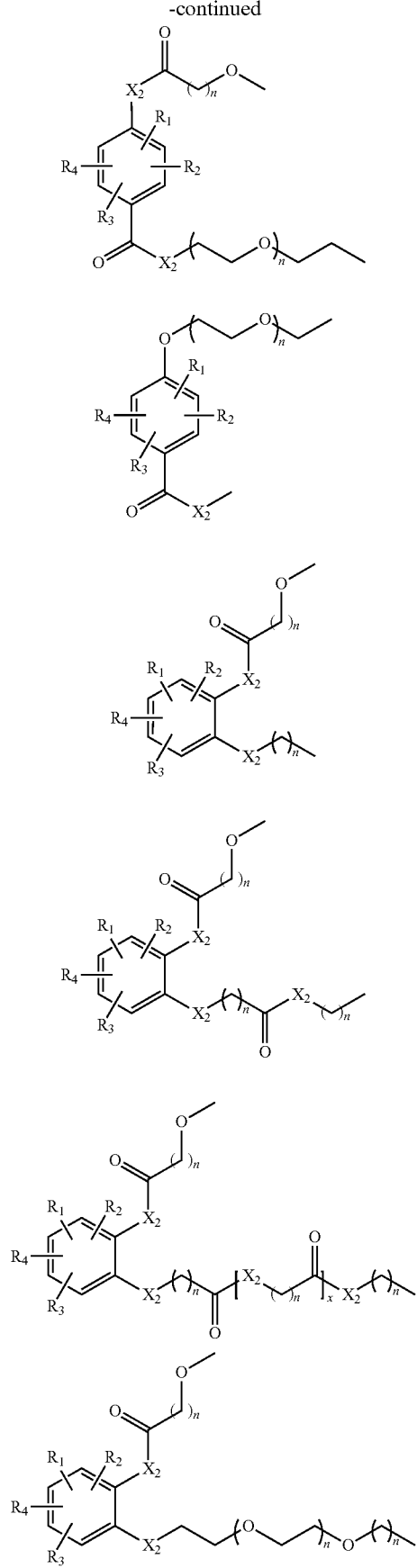
-continued
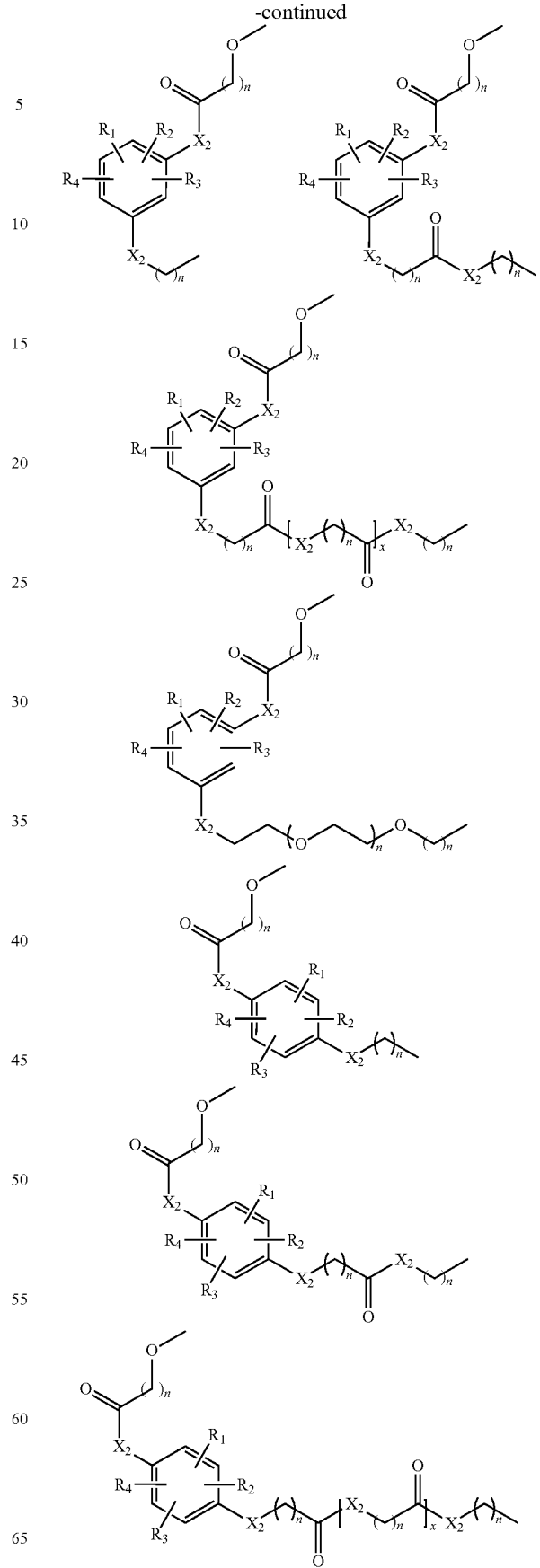

-continued

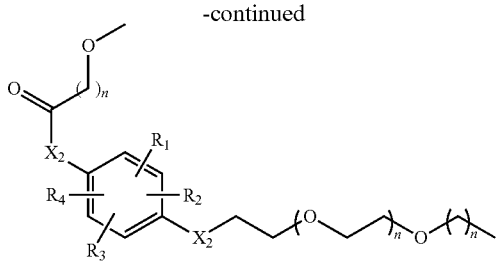

wherein
$X_2$=O or NH,
n=1-10,
x=1-10,
R is independently selected from H; alkyl; cycloalkyl; aryl,
$R_1$, $R_2$, $R_3$ and $R_4$ are independently selected from H; hydroxyl; —B(OR$^{1*}$)(OR$^{1**}$)
  wherein R$^{1*}$ and R$^{1**}$ are independently selected from H; alkyl; lower alkyl; cycloalkyl; aryl; heteroaryl; alkenyl; heterocycle; halides; nitro; —C(O)OR$^{2*}$
    wherein R$^{2*}$ is selected from H, alkyl, cycloalkyl and aryl; —C(O)NR$^{3}$R$^{3*}$,
      wherein R$^{3}$ and R$^{3*}$ are independently selected from H, alkyl, cycloalkyl and aryl; —CH$_2$C(O)R$_a$,
        wherein R$_a$ is selected from —OH, lower alkyl, cycloalkyl; aryl, -lower alkyl-aryl, -cycloalkyl-aryl; or —NR$_b$R$_c$,
        where R$_b$ and R$_c$ are independently selected from H, lower alkyl, cycloalkyl; aryl or -lower alkyl-aryl; —C(O)R$_d$,
          wherein R$_d$ is selected from lower alkyl, cycloalkyl; aryl or -lower alkyl-aryl; or -lower alkyl-OR$_e$,
            wherein R$_e$ is a suitable protecting group or OH group,
$R_5$, $R_6$, and $R_7$ are independently selected from H; nitro; cyano; halides; alkyl; cycloalkyl; aryl and C(O)OR$^{4*}$,
  wherein R$^{4*}$ is selected from H, alkyl, cycloalkyl and aryl; —C(O)NR$^{5}$R$^{5*}$,
    wherein R$^{5}$ and R$^{5*}$ are independently selected from H, alkyl; cycloalkyl and aryl,
$R_8$ and $R_9$ are independently selected from H; halides; alkyl; cycloalkyl and aryl,
$R_{10}$ is selected from H; nitro; cyano; halides; alkyl; cycloalkyl; aryl and C(O)OR$^{6*}$,
  wherein R$^{6*}$ is selected from H, alkyl, cycloalkyl and aryl; —C(O)NR$^{7}$R$^{7*}$,
    wherein R$^{7}$ and R$^{7*}$ are independently selected from H, alkyl; cycloalkyl and aryl,
$R_{11}$, $R_{12}$, $R_{13}$ and $R_{14}$ are independently selected from H; alkyl; cycloalkyl; aryl and —SO$_3$R$^{8*}$,
  wherein R$^{8*}$ is selected from H; Na,
$R_{15}$ and $R_{16}$ are independently selected from H; alkyl; cycloalkyl; aryl and C(O)OR$^{9*}$
  wherein R$^{9*}$ is selected from H, alkyl, cycloalkyl and aryl; —C(O)NR$^{10}$R$^{10*}$,
    wherein R$^{10}$ and R$^{10*}$ are independently selected from H, alkyl; cycloalkyl and aryl,
$R_{17}$ and $R_{18}$ are independently selected from H; halides; alkyl; cycloalkyl and aryl,
$R_{19}$, $R_{20}$, and $R_{21}$ are independently selected from H; alkyl; aryl and C(O)OR$^{11*}$,
  wherein R$^{11*}$ is selected from H, alkyl; cycloalkyl and aryl; —C(O)NR$^{12}$R$^{12*}$,
    wherein R$^{12}$ and R$^{12*}$ are independently selected from H, alkyl; cycloalkyl and aryl,
$R_{22}$ is selected from alkyl; cycloalkyl; aryl; —NR$^{13*}$R$^{13**}$,
  wherein R$^{13*}$ and R$^{13}$ are independently selected from H, alkyl; cycloalkyl; aryl and —COR$^{14*}$,
    wherein R$^{14***}$ is alkyl; cycloalkyl and aryl,
$R_{23}$, $R_{24}$, $R_{25}$, $R_{26}$ and $R_{27}$ are selected from H; alkyl; lower alkyl; cycloalkyl; aryl; heteroaryl; alkenyl; heterocycle; halides; OR$^{15*}$,
  wherein R$^{15*}$ is selected from H, alkyl; cycloalkyl and aryl,
wherein the modification is a linchpin directed modification or protein directed modification or Fn1 accelerated kinetic labeling by Fn2, and
wherein the protein obtained by the method is reacted with sodium cyanoborohydride for the protein cyclization.

11. The method as claimed in claim 10, wherein in the multifunctional chemical agent, Fn1 reacts reversibly or irreversibly with a rate of reaction $k_1$ and Fn2 reacts irreversibly with a rate of reaction $k_2$ in an intramolecular reaction,
  wherein Fn1 and Fn2 are selected such that the rate of reaction is $k_1 \gg k_2$, and
  wherein the method is for a single site labeling of the protein resulting in one or more of conjugation at a backbone residue or N-terminus, late stage modification of the protein, dual site labeling of the protein, single site labeling in a mixture of proteins, protein-protein conjugation and protein cyclization.

12. The method as claimed in claim 11, wherein the site for selective modification of the protein is selected from Lysine, Histidine, Cysteine, Aspartic acid or Glutamic acid, Tyrosine, Arginine and Methionine of the native protein or any functional biological molecule,
  wherein Fn1 reacts with either Lysine or Cystine, and
  wherein Fn2 reacts with Lysine, Histidine, Cysteine, Aspartic acid, Glutamic acid, Tyrosine, Arginine or Methionine.

13. The method as claimed in claim 10, wherein the ratio of the protein to the multifunctional agent is 1:1 to 1:100.

14. The method as claimed in claim 10, wherein the method is carried out at a temperature 4-37° C.

15. The method as claimed in claim 10, wherein the method is carried at a pH 4-10.

16. The method as claimed in claim 10, wherein the method is carried out for 10 minutes to 72 hours.

17. The method as claimed in claim 10, wherein the modified protein is further purified from the protein mixture by using a hydrazide-activated resin.

* * * * *